US008759259B2

(12) United States Patent
Kwon et al.

(10) Patent No.: US 8,759,259 B2
(45) Date of Patent: Jun. 24, 2014

(54) COMPOSITIONS AND METHODS FOR PRODUCING CYCLIC PEPTOID LIBRARIES

(75) Inventors: Yong-Uk Kwon, Seoul (KR); Thomas Kodadek, Jupiter, FL (US)

(73) Assignee: The Board of Regents of the University of Texas System, Austin, TX (US)

(*) Notice: Subject to any disclaimer, the term of this patent is extended or adjusted under 35 U.S.C. 154(b) by 462 days.

(21) Appl. No.: 12/905,605

(22) Filed: Oct. 15, 2010

(65) Prior Publication Data

US 2011/0092384 A1 Apr. 21, 2011

Related U.S. Application Data

(60) Provisional application No. 61/252,333, filed on Oct. 16, 2009.

(51) Int. Cl.
C40B 50/14 (2006.01)
C07K 5/00 (2006.01)

(52) U.S. Cl.
USPC ........ 506/30; 506/9; 506/18; 506/32; 506/40; 506/42; 530/317; 530/321; 530/333; 530/323; 530/334

(58) Field of Classification Search
USPC ........ 506/9, 18, 30, 32, 40, 42; 530/317, 321, 530/333, 323, 334
See application file for complete search history.

(56) References Cited

U.S. PATENT DOCUMENTS

| | | | |
|---|---|---|---|
| 4,789,628 A | 12/1988 | Nayak | 435/7 |
| 5,011,771 A | 4/1991 | Bellet et al. | 435/7.94 |
| 5,149,626 A | 9/1992 | Fleming | 435/7.9 |
| 5,510,640 A | 4/1996 | Hozumi et al. | 568/640 |
| 5,617,060 A | 4/1997 | Wilson et al. | 330/129 |
| 5,705,614 A | 1/1998 | Ring | 530/387.3 |
| 5,719,060 A | 2/1998 | Hutchens et al. | 436/174 |
| 6,153,596 A | 11/2000 | Liotta et al. | 514/44 A |
| 6,197,599 B1 | 3/2001 | Chin et al. | 436/518 |
| 6,225,047 B1 | 5/2001 | Hutchens et al. | 435/5 |
| 6,297,059 B1 | 10/2001 | Song et al. | 436/501 |
| 6,306,643 B1 | 10/2001 | Galtalen et al. | 435/287.2 |
| 6,329,209 B1 | 12/2001 | Wagner et al. | 436/518 |
| 6,344,330 B1 | 2/2002 | Ellman et al. | 435/7.1 |
| 6,344,334 B1 | 2/2002 | Ellman et al. | 435/7.1 |
| 6,365,347 B1 | 4/2002 | Murray et al. | 435/6 |
| 6,365,418 B1 | 4/2002 | Wagner et al. | 436/518 |
| 6,406,921 B1 | 6/2002 | Wagner et al. | 436/518 |
| 6,461,515 B1 | 10/2002 | Safir et al. | 210/656 |
| 6,465,183 B2 | 10/2002 | Wolber | 435/6 |
| 6,465,430 B1 | 10/2002 | Dower et al. | 514/13 |
| 6,475,391 B2 | 11/2002 | Safir et al. | 210/656 |
| 6,800,728 B2 | 10/2004 | Schwartz | 530/345 |
| 7,091,046 B2 | 8/2006 | Monforte | 436/173 |
| 7,504,364 B2 | 3/2009 | Carlson | 506/30 |
| 7,504,365 B2 | 3/2009 | Carlson | 506/30 |
| 2002/0006620 A1 | 1/2002 | Short | 435/6 |
| 2002/0018749 A1 | 2/2002 | Hudson et al. | 424/1.49 |
| 2002/0022227 A1 | 2/2002 | Short | 435/6 |
| 2002/0055125 A1 | 5/2002 | Charych et al. | 435/7.5 |
| 2002/0055186 A1 | 5/2002 | Barry et al. | 436/518 |
| 2002/0098493 A1 | 7/2002 | Nathan | 435/6 |
| 2002/0137106 A1 | 9/2002 | Leung et al. | 435/7.9 |
| 2002/0168699 A1 | 11/2002 | Thompson et al. | 435/7.92 |
| 2002/0192690 A1 | 12/2002 | Dower et al. | 435/6 |
| 2003/0003516 A1 | 1/2003 | Robinson et al. | 435/7.9 |
| 2003/0017508 A1 | 1/2003 | Charych et al. | 435/7.9 |
| 2003/0092009 A1 | 5/2003 | Palm | 435/6 |
| 2003/0153014 A1 | 8/2003 | Shen et al. | 435/7.9 |
| 2003/0207467 A1 | 11/2003 | Snyder et al. | 436/518 |
| 2004/0161748 A1 | 8/2004 | He et al. | 435/6 |
| 2004/0161798 A1 | 8/2004 | Kodadek | 435/7.1 |
| 2004/0171068 A1 | 9/2004 | Wehland et al. | 435/7.1 |
| 2004/0241751 A1 | 12/2004 | Wagner et al. | 435/7.1 |
| 2005/0048566 A1 | 3/2005 | Delisi et al. | 435/7.1 |
| 2005/0048580 A1 | 3/2005 | Labaer et al. | 435/7.1 |

FOREIGN PATENT DOCUMENTS

| | | |
|---|---|---|
| EP | 0268296 | 5/1988 |
| EP | 0317804 | 5/1989 |
| EP | 0491362 | 6/1992 |
| EP | 0586618 | 7/1997 |
| EP | 0818467 | 1/1998 |
| EP | 1319954 | 6/2003 |
| GB | 2404734 | 2/2005 |
| WO | WO 98/59360 | 12/1998 |
| WO | WO 99/51773 | 10/1999 |
| WO | WO 00/56934 | 9/2000 |
| WO | WO 01/57530 | 8/2001 |
| WO | WO 01/69258 | 9/2001 |
| WO | WO 01/88538 | 11/2001 |
| WO | WO 01/98534 | 12/2001 |
| WO | WO 02/18648 | 3/2002 |

(Continued)

OTHER PUBLICATIONS

Gocke et al., "Supplemental Data—Isolation of antagonists of antigen-specific autoimmune T cell proliferation," *Chemistry & Biology*, 16:1133-1139, 2009.
Lindstrom and Robinson, "Fishing for biomarkers with antigen mimics," *Cell*, 144:13-15, 2011.
Reddy et al., "Identification of candidate IgG biomarkers for Alzheimer's disease via combinatorial library screening," *Cell*, 144:132-142, 2011.
"Biomarker Discovery: Expression difference mapping™ applications," www.ciphergen.com/techapps/pc/apps/biomarker/edm.asp, Sep. 28, 2004.
"Biomarker Discovery: Interaction discovery mapping™ application," www.ciphergen.com/techapps/pc/apps/biomarker/idm.asp, Sep. 28, 2004.
"Leading the way in biomarker research: Accelerating biomarker discovery assays," CIPHERGEN® The ProteingChip® Company, Product Information Sheet, 2004.

(Continued)

*Primary Examiner* — Teresa Wessendorf
(74) *Attorney, Agent, or Firm* — Parker Highlander PLLC

(57) ABSTRACT

Embodiments of the invention are directed to a one-bead-two-compound method for the creation of encoded cyclic peptoid libraries. This scheme is useful for the creation of cyclic peptoid microarrays since only the cyclic peptoid, not the linear encoding molecule, contains an attachment residue and thus can be spotted onto an activated substrate.

13 Claims, 19 Drawing Sheets

(56) References Cited

FOREIGN PATENT DOCUMENTS

| WO | WO 02/31510 | 4/2002 |
|---|---|---|
| WO | WO 02/46757 | 6/2002 |
| WO | WO 02/063299 | 8/2002 |
| WO | WO 02/073209 | 9/2002 |
| WO | WO 03/050544 | 6/2003 |
| WO | WO 03/072827 | 9/2003 |
| WO | WO 03/074722 | 9/2003 |
| WO | WO 03/074990 | 9/2003 |
| WO | WO 2004/005319 | 1/2004 |
| WO | WO 2004/005477 | 1/2004 |
| WO | WO 2005/007677 | 1/2005 |
| WO | WO 2006/124644 | 11/2006 |

OTHER PUBLICATIONS

"ProteinChip® Technology: Array technology," www.ciphergen.com/techapps/pc/tech/arrays.asp, Sep. 28, 2004.

"Unraveling biological pathways using the Interaction Discovery Mapping™ platform," CIPHERGEN® The ProteingChip® Company, Product Information Sheet, 2004.

Alluri et al., "Isolation of protein ligands from large peptoid libraries," *J. Am. Chem. Soc.*, 125:13995-14004, 2003.

Alluri, et al., "Isolation and characterization of coactivator-binding peptoids from a combinatorial library," *Mol. BioSystems*, 2:568-79, 2006.

Astle et al., "A VEGFR2 antagonist and other peptoids evade immune recognition," *Int J Pept Res Ther*, 14:223-227, 2008.

Bachhawat-Sikder and Kodadek, "Mixed-element capture agents: a simple strategy for the construction of synthetic, high-affinity protein capture ligands," *J. Am. Chem. Soc.*, 125:9550-9551, 2003.

Baldini et al., "Pattern-based detection of different proteins using an array of fluorescent protein surface receptors," *J. Am. Chem. Soc.*, 126:5656-5657, 2004.

Borman, "Combinatorial chemistry," *Chem. &Eng. News*, 75: 43-62,1997.

Brenner et al., "Gene expression analysis by massively parallel signature sequencing (MPSS) on microbead arrays," *Nature Biotechnology*, 18:630-634, 2000.

Brocchini et al., "A Combinatorial Approach for Polymer Design," *J. Am. Chem. Soc.*, 119:4553-4554, 1997.

Burger and Still, "Simple structural requirements for sequence-selective peptide receptors? Tripeptide binding by a podand ionophore," *J. Org. Chem.*, 62:4785-4790, 1997.

Burkoth et al., "Toward the synthesis of artificial proteins: the discovery of an amphiphilic helical peptoid assembly," *Chem. Biol.*, 9:647-654, 2002.

Burton, "Phage display," *Immunotechnology* 1:87-94,1995.

Caputo et al., "Methods for on-chip protein analysis," *Analytical Biochemistry*, 321:116-124, 2003.

Carins et al., "A novel bacterial vector system for monitoring protein-protein interactions in the cAMP-dependent protein kinase complex," *Gene*, 185:5-9, 1997.

Cekaite et al., "Analysis of the humoral immune response to immunoselected phage-displayed peptides by a microarray-based method," *Proteomics*, 4:2572-2582, 2004.

Chen et al., "Fluorescent, sequence-selective peptide detection by synthetic small molecules," *Science*, 279:851-853, 1998.

Cheng et al., "Sequence-selective peptide binding with peptido-A. B-trans-steroidal receptor selected from an encoded combinatorial receptor library," *J. Amer. Chem. Soc.*, 118:1813-1814, 1996.

Cho et al., "Cyclic and linear oligocarbamate ligands for human thrombin," *Bioorg Med Chem* 7, 1171-1179, 1999.

Conrads et al., "Cancer diagnosis using proteomic patterns," *Expert. Rev. Mol.Diagn.*, 3:411-420, 2003.

Conrads et al., "High-resolution serum proteomic features for ovarian cancer detection," *Endocrine-Related Cancer*, 11:163-178, 2004.

Conrads et al., "Proteomic patterns as a diagnostic tool for early-stage cancer: a review of its progress to a clinically relevant tool," *Mol. Diagn.* 8:77-85, 2004.

Cox et al., "Integrating gene and protein expression data: pattern analysis and profile mining," *Methods*, 35:303-314, 2005.

Cussac et al., "A Sos-derived peptidimer blocks the Ras signaling pathway by binding both Grb2 SH3 domains and displays antiproliferative activity," *FASEB J.*, 13:31-38, 1999.

Davies and Riechmann, "Single antibody domains as small recognition units: design and in vitro antigen selection of camelized, human VH domains with improved protein stability," *Protein Engineering*, 9(6):531-537, 1996.

Deinhofer et al., "Microarrayed allergens for IgE profiling," *Methods*, 32:249-254, 2004.

Demir et al., "Proteome analysis of human mesothelial cells during epithelial to mesenchymal transitions induced by shed menstrual effluent," *Proteomics*, 4:2608-2623, 2004.

Dinarello, "Interleukin-1 beta, interleukin-18, and the interleukin-1 beta converting enzyme," *Ann. N.Y. Acad. Sci.*, 856:1-11, 1998.

Dong et al., "Molecular forceps from combinatoral libraries prevent the farnesylation of Ras by binding to its carboxyl terminus," *Chem. & Biol.*, 6:133-144, 1999.

Dostmann et al., "Delineation of selective cyclic GMP-dependent protein kinase Ialpha substrate and inhibitor peptides based on combinatorial peptide libraries on paper," *Pharmacol. Ther.*, 82:373-387, 1999.

Dove et al., "Conversion of the w subunit of *Eschericia coli* RNA polymerase into a transcriptional activator or activation target," *Gene and Development*, 12:745-754, 1998.

Eichler et al., "Peptide, peptidomimetic, and organic synthetic combinatorial libraries," *Med Res Rev.*, 15(6):481-96, 1995.

Elgersma et al., "Transformation of the amyloidogenic peptide amylin into its corresponding peptoid and retropeptoid: Access to both an amyloid inhibitor and templae for self-assembled supramolecular tapes," *Bioorganic and Medicinal Chemistry Letters*, 17:1837-1842, 2007.

Fairbrother et al. "Novel peptides selected to bind vascular endothelial growth factor target the receptor-binding site," *Biochemistry*, 37:17754-17764, 1998.

Fancy and Kodadek, "Chemistry for the analysis of protein-protein interactions: rapid and efficient cross-linking triggered by long wavelength light," *Proc. Natl. Acad. Sci., USA*, 96:6020-6024, 1999.

Figliozzi et al., "Synthesis of N-substituted glycine peptoid libraries,"*Methods Enzymol.*, 267:437-447, 1996.

Fodor et al., "Light-directed, spatially addressable parallel chemical synthesis," *Science*, 251:767-773, 1991.

Forterre et al., "Protein profiling of urine from dogs with renal disease using ProteinChip analysis," *J. Vet. Diagn. Invest.*, 16:271-277, 2004.

Gallop et al., "Applications of combinatorial technologies to drug discovery. 1. Background and peptide combinatorial libraries," *J. Med. Chem.*, 37(9):1233-1251, 1994.

Gocke et al., "Isolation of antagonists of antigen-specific autoimmune T cell proliferation," *Chem. and Biol.*, 16(11):1133-1139, 2009.

Gordon et al., "Applications of combinatorial technologies to drug discovery. 2. Combinatorial organic synthesis, library screening strategies, and future directions," *J. Med. Chem.*, 37(10):1385-401, 1994.

Griffiths and Duncan, "Strategies for selection of antibodies by phage," *Curr. Opin. Biotechnol.*, 9:102-108, 1998.

Grow et al., "New biochip technology for label-free detection of pathogens and their toxins," *J. Microbiological Methods*, 53:221-233, 2003.

Gruden et al., "Differential neuroimmune markers to the onset of Alzheimer's disease neurodegeneration and dementia: Autoantibodies to $A\beta_{(25-35)}$ oligomers, S100b and neurotransmitters," *Journal of Neuroimmunology*, 186:181-192, 2007.

Grumwald et al., "In situ assembly of macromolecular complexes triggered by light," *PNAS*, 107(14):6146-6151, 2010.

Hajduk et al., "Discovery of potent nonpeptide inhibitors of stromelysin using SAR by NMR," *J. Amer. Chem. Soc.*, 119:5818-5827, 1997.

Han and Kodadek, "Peptides selected to bind the Gal80 repressor are potent transcriptional activation domains in yeast," *J. Biol. Chem.*, 275(20):14979-14984, 2000.

(56) References Cited

OTHER PUBLICATIONS

Harland and Weintraub, "Translation of mRNA injected into *Xenopus* oocytes is specifically inhibited by antisense RNA," *J. Cell Biol.* 101:1094-1099, 1985.
He et al.,"Transformation of wheat (*Triticum aestivum* L.) through electroporation of protoplasts," *Plant Cell Reports*, 14:192-196, 1994.
Heine et al., "Synthesis and screening of peptoid arrays on cellulose membranes," *Tetrahedron*, 59:9919-9930, 2003.
Hiemstra et al., "Antigen arrays in T cell immunology," *Current Opinion in Immunology*, 12:80-84, 2000.
Hoffmann et al., "Transformation of a biologically active peptide into peptoid analogs while retaining biological activity," *Protein & Peptide Letters*, 13:829-833, 2006.
Horn, et al., "Incorporation of chemoselective functionalities into peptoids via solid-phase submonomer synthesis," *Bioconj. Chem.*, 15:428-35, 2004.
Hossain and Schneider, "Sequence-selective evaluation of peptide side-chain interaction. New artificial receptors for selective recognition in water", *J. Amer. Chem. Soc.*, 120:11208-11209, 1998.
Howard et al., "Identification of collagen-binding proteins in *Lactobacillus* spp. with surface-enhanced laser desorption/ionization-time of flight ProteinChip technology," *Applied and Environmental Microbiology*, 66:4396-4400, 2000.
Hu et al,"Sequence requirements for coiled-colis: Analysis with lambda Repressor-GCN4 leucine zipper fusions," *Science*, 250:1400-1403, 1990.
Hu, "Repressor fusions as a tool to study protein-protein interactions," *Structure* 3:431-433, 1995.
Huang et al., "Enhanced protein profiling arrays with ELISA-based amplification for high-throughput molecular changes of tumor patients' plasma," *Clinical Cancer Research*, 10:598-609, 2004.
Huang et al., "High-Throughput Genomic and Proteomic Analysis Using Microarray Technology," *Clinical Chemistry*, 47:1912-1916, 2001.
Huber et al., "Comparison of Proteomic and Genomic Analyses of the Human Breast Cancer Cell Line T47D and the Antiestrogen-resistant Derivative T47D-r," *Molecular & Cellular Proteomics 3.1*, 3:43-55, 2004.
Hudelist et al., "Use of high-throughput protein array for profiling of differentially expressed proteins in normal and malignant breast tissue," *Breast Cancer Research and Treatment*, 86:281-291, 2004.
Hueber et al., "Autoantibody profiling for the study and treatment of autoimmune disease," *Arthritis Res.*, 4(5): 290-295, 2002.
International Search Report and Written Opinion issued in PCT/US2010/052837, dated Jan. 27, 2011.
Ivanov et al., "Antibodies Immobilized as Arrays to Profile Protein Post-translation Modifications in Mammalian Cells," *Molecular & Cellular Proteomics 3.8*, 3:788-795, 2004.
Jappelli and Brenne, "Interaction between cAMP-dependent protein kinase catalytic subunit and peptide inhibitors analyzed with λ Repressor fusions," *J. Mol. Bio.*,. 259:575-578, 1996.
Jenkins and Pennington, "Arrays of protein expresion profiling: Towards a viable alternative to two-dimensional gel electrophoresis?" *Proteomics*, 1:13-29, 2001.
Kanemitsu and Kanie, "Recent developments in oligosaccharide synthesis: tactics, solid-phase synthesis and library synthesis," *Comb Chem High Throughput Screen*, 5(5):339-360, 2002.
Kaplan et al., "A new mechanism for immunologic initiation of asthma," *PNAS*, 102(5):1267-1268, 2005.
Kiessling et al., "Synthetic multivalent ligands in the exploration of cell-surface interactions," *Curr. Opin. Chem. Biol.*, 4:696-703, 2000.
Kim et al.," Photo-induced protein cross-linking mediated by palladium porphyrins," *J. Amer. Chem. Soc.*, 121:11896-11897, 1999.
Kirshenbaum et al., "Sequence-specific polypeptoids: a diverse family of heteropolymers with stable secondary structure," *Proc. Natl. Acad. Sci., USA*, 95:4303-4308, 1998.
Kitov et al., "Shiga-like toxins are neutralized by tailored multivalent carbohydrate ligands," *Nature*, 403:669-672, 2000.

Kodadek, "Development of protein-detecting microarrays and related devices," *Trends Biochem. Sci.*, 27(6):295-300, 2002.
Kodadek, "Protein microarrays: prospects and problems," *Chem. Biol.*, 8:105-115, 2001.
Koehler et al., "Discovery of an inhibitor of a transcription factor using small molecule microarrays and diversity-oriented synthesis," *J. Amer. Chem. Soc.*, 125:8420-8421, 2003.
Kuruvilla et al., "Dissecting glucose signaling with diversity-oriented synthesis and small-molecule microarrays," *Nature*, 416:653-657, 2002.
Kwon and Kodadek, "Encoded combinatorial libraries for the construction of cyclic peptoid microarrays," *Chem. Commun.*, pp. 5704-5706, 2008.
Kwon and Kodadek, "Encoded combinatorial libraries for the construction of cyclic peptoid microarrays," *Chem. Comm.*, 44:S1-S21, 2008.
Ladbury et al., "Measurement of the binding of tyrosyl phosphopeptides to SH2 domains: a reappraisal.," *Proc. Natl. Acad. Sci., USA*, 92:3199-3203, 1995.
Le Bihan et al., "Evaluation of an integrated strategy for proteomic profiling of skeletal muscle," *Proteomics*, 4:2739-2753, 2004.
Leak et al., "Proteomic analysis of lymph," *Proteomics*, 4:753-765, 2004.
Lee et al., "Protein patterning on silicon-based surface using background hydrophobic thin film," *Biosensors and Bioelectronics*, 18:437-444, 2003.
LePlae et al., "Tolerence of Acyclic Residues in the beta-Peptide 12-Helix: Access to Diverse Side-Chain Arrays for Biological Applications," *J. Amer. Chem. Soc.*, 124:6820-6821, 2002.
Li et al., "Photolithographic synthesis of cyclic peptide arrays using a differential deprotection strategy," *Chem. Commun.*, 581-583, 2005.
Li et al., "Photolithographic Synthesis of Peptoids," *J. Am. Chem. Soc.*, 126:4088-4089, 2004.
Ligler et al., "Array biosensor for detection of toxins," *Anal. Bioanal. Chem.*, 377:469-477, 2003.
Lin et al., "Profiling of cytokine expression by biotin-labeled-based protein arrays," *Proteomics*, 3:1750-1757, 2003.
Liu et al., "Analysis of Prostate Cancer by Proteomics using Tissue Specimens," *J. Urology*, 173:73-78, 2005.
Lopez et al., "Serum Autoantibodies in Patients with Alzheimer's Disease and Vascular Dementia and Nondemented Control Subjects," *Stroke*, 23:1078-1083,1992.
MacBeath, et al., "Printing small molecules as microarrays and detecting protein-ligand interactions en masse," *J. Am. Chem. Soc.*, 121:7967-8, 1999.
Maly et al., "Combinatorial target-guided ligand assembly: identification of potent subtype-selective c-Src inhibitors," *Proc. Natl. Acad. Sci., USA*, 97:2419-2424, 2000.
Martin, "Preorganization in biological systems: Are conformational constraints worth the energy?" *Pure Appl. Chem.*, 79:193-200, 2007.
Melcher and Xu, "Ga180-Ga180 interaction on adjacent Gal4p binding sites is required for complete GAL gene repression," *EMBO J.* 20:841-851, 2001.
Melle et al., "A technical triade for proteomic identification and characterization of cancer biomarkers," *Cancer Research*, 64:4099-4104, 2004.
Meloen et al., "Mimotopes: realization of an unlikely concept," *J. Mol. Recognition*, 13:352-359, 2000.
Merritt et al., "Characterization and crystal structure of a high-affinity pentavalent receptor-binding inhibitor for cholera toxin and *E. coli* heat-labile enterotoxin," *J. Amer. Chem. Soc.*, 124:8818-8824, 2002.
Mezzasoma et al., "Antigen Microarrays for Serodiagnosis of Infectious Diseases," *Clinical Chemistry*, 48:121-130, 2002.
Mikolajczyk et al., "High yield, site-specific coupling of N-terminally modified beta-lactamase to a proteolytically-derived single-sulfhydryl murine Fab," *Biooconj. Chem.*, 5:636-646, 1994.
Motoori et al., "Prediction of recurrence in advanced gastric cancer patients after curative resection by gene expression profiling," *Int. J. Cancer*, 114:963-968, 2005.

(56) References Cited

OTHER PUBLICATIONS

Neuman de Vegvar and Robinson, "Microarray profiling of antiviral antibodies for the development of diagnostics, vaccines, and therapeutics," *Clinical Immunology*, 111:196-201, 2004.

O et al., "Peptides mimicking sialyl-Lewis A isolated from a random peptide library and peptide array," *Ann N Y Acad Sci*, 886:276-279, 1999.

O'Brian-Simpson et al., "Polymerization of unprotected peptides: A view towards synthetic peptide vaccines," *J. Amer. Chem. Soc.*, 119:1183-1188, 1997.

Olejniczak et al., "Stromelysin inhibitors designed from weakly bound fragments: effects of linking and cooperativity," *J. Amer. Chem. Soc.*, 119:5828-5832, 1997.

Oliver et al., "Multiplexed Analysis of Human Cytokines by Use of the FlowMetrix System," *Clinical Chemistry*, 44:2057-2060, 1998.

Ornstein et al., "Serum Proteomic Profiling can Discriminate Prostate Cancer From Benign Prostates in Men with Total Prostrate Specific Antigen Levels Between 2.5 and 15.0 NG/ML," *J. Urology*, 172:1302-1305, 2004.

Ostergaard and Holm, "Peptomers: A versatile approach for the preparation of diverse combinatorial peptidomimetic bead libraries," *Mol. Divers.*, 3:17-27, 1997.

Park and Raines "Genetic selection for dissociative inhibitors of designated protein-protein interactions," *Nature Biotechnol.*, 18, 847-851, 2000.

Phizicky and Fields, "Protein-protein interactions: methods for detection and analysis," *Microbiological Reviews*, 59(1):94-123, 1995.

Quintana et al., "Functional immunomics: microarray analysis of IgG autoantibody repertoires predicts the future response of mice to induced diabetes," *Proc. Nat. Acad. Sci. USA*, 101:14615-14621, 2004.

Rader and Barbas, "Phage display of combinatorial antibody libraries," *Curr. Opin. Biotechnol.*, 8:503-508, 1997.

Radulovic et al., "Informatics Platform for Global Proteomic Profiling and Biomarker Discovery Using Liquid Chromatography-Tandem Mass Spectrometry," *Molecular & Cellular Proteomics 3.10*, 3:984-997, 2004.

Reddy and Kodadek, "Protein "fingerprinting" in complex mixtures with peptoid microarrays," *Proc. Nat. Acad. Sci. USA* 102, 12672-12677, 2005.

Reddy et al., "Transformation of low-affinity lead compounds into high-affinity protein capture agents," *Chem. Biol.*, 11:1127-1137, 2004.

Reineke et al., "Identification of distinct antibody epitopes and mimotopes from a peptide array of 5520 randomly generated sequences," *J. Immunol. Methods*, 267:37-51, 2002.

Robinson et al., "Autoantigen microarrays for multiplex characterization of autoantibody responsesm," *Nature Medicine*, 8:295-301, 2002.

Robinson et al., "Protein and Peptide Array Analysis of Autoimmune Disease," *BioTechniques*, 33:S66-S69, 2002.

Robinson et al., "Protein microarrays guide tolerizing DNA vaccine treatment of autoimmune encephalomyelitis," *Nature Biotechnology*, 21:1033-1039, 2003.

Rose et al., "Natural peptides as building blocks for the synthesis of large protein-like molecules with hydrazone and oxime linkages," *Bioconj. Chem.* 7:552-556, 1996.

Sasaki et al., "A new application of a peptide library to identify selective interaction between small peptides in an attempt to develop recognition molecules toward protein surfaces," *Tetrahedron Letters*, 37:85-88, 1996.

Schneider et al., "Scaffold-hopping: by topological pharmacophore search: a contribution to virtual screening," *Angew Chem Int Ed Engl.*, 38:2894-2896, 1999.

Schreiber, "Target-oriented and diversity-oriented organic synthesis in drug discovery," *Science*, 287(5460), 1964-1969, 2000.

Scott, et al., "Production of cyclic peptides and proteins in vivo," *Proc. Natl. Acad. Sci. USA*, 96:13638-13643, 1999.

Shao et al, "Sequence-selective receptors of peptides. A simple molecular design for construction of large combinatorial libraries of receptors," *J. Org. Chem.*, 61:6086-6087, 1996.

Shepard et al., "Array-based binary analysis for bacterial typing," *Anal. Chem.*, 77:319-326, 2005.

Shuker et al., "Discovering high-affinity ligands for proteins: SAR by NMR," *Science*, 274:1531-1534, 1996.

Simon, et al., "Peptoids: a modular approach to drug discovery," *Proc. Natl. Acad. Sci. USA*, 89:9367-71, 1992.

Staub et al., "Systematic identification of immunoreceptor tyrosine-based inhibitory motifs in the human proteome," *Cellular Signalling*, 16:435-456, 2004.

Still, "Discovery of sequence-selective peptide binding by synthetic receptors using encoded combinatorial libraries," *Acc. Chem. Res.*, 29:155-163, 1996.

Stoll et al., "Chalcone derivatives antagonize interactions between the human oncoprotein MDM2 and p53," *Biochemistry*, 40:336-344, 2001.

Sydor and Nock, "Protein expression profiling arrays: tools for the multiplexed high-throughput analysis of proteins," *Proteome Science*, 1:1-7, 2003.

Tannapfel et al., "Identification of novel proteins associated with hepatocellular carcinomas using protein microarrays," *J. of Pathology*, 238-249, 2003.

Terryberry et al., "Autoantibodies in Neurogdegenerative Diseases: Antigen-Specific Frequencies and Intrathecal Analysis," *Neurobiology of Aging*, 19:205-216.

Terskikh et al., "'Peptabody3 : A new type of high avidity binding protein," *Proc. Natl. Acad. Sci., USA*, 94:1663-1668, 1997.

Thoma et al., "Nanomolar E-selectin inhibitors: 700-fold potentiation of affinity by multivalent ligand presentation," *J. Amer. Chem. Soc.*, 123:10113-10114, 2001.

Thompson and Ellman, "Synthesis and Applications of Small Molecule Libraries," *Chem. Rev.*, 96(1):555-600, 1996.

Udugamasooriya et al., "The pharmacore of a peptoid VEGF receptor 2 antagonist includes both side chain and main chain residues," *Bioorganic & Medicinal Chemistry Letters*, 18:5892-5894, 2008.

Udugamasooriya, et al., "A peptoid "antibody surrogate" that antagonizes VEGF receptor 2 activity," *J. Amer. Chem. Soc.*, 130:5744-5752, 2008.

Usui et al., "Peptide Arrays with Designed Secondary Structures for Protein Characterization Using Fluorescent Fingerprint Patterns," *Biopolymers (Peptide Science)*, 76:129-139, 2004.

Valafar, "Pattern recognition techniques in microarray data analysis: a survey," *Ann. N.Y. Acad. Sci.*, 980:41-64, 2002.

Veenstra and Com-ads, "Serum protein fingerprinting," *Curr. Opin. Mol. Therapeutics*, 15:584-593, 2003.

Veenstra et al., "Proteomic patterns for early cancer detection," *DDT*, 9:889-897, 2004.

Venkatesh, et al., "Prevention of passively transferred experimental autoimmune myasthenia gravis by a phage library-derived cyclic peptide," *Proc. Natl. Acad. Sci. USA*, 97:761-6, 2000.

Vignali, "Multiplexed particle-based flow cytometric assays," *J. of Immunol. Methods*, 243:243-255, 2000.

Wang et al., "Autoantibody Signatures in Prostate Cancer," *New Eng. J. Med.*, 353:1224-1235, 2005.

Weinberger et al., "Surface-enhanced laser desorption-ionization retentate chromatography mass spectrometry (SELDI-RC-MS): a new method for rapid development of process chromatography conditions," *J. Chromatography B*, 782:307-316, 2002.

Winssinger et al., "Profiling protein function with small molecule microarrays," *PNAS*, 99:11139-11144, 2002.

Wong et al., "Protein profiling of cervical cancer by protein-biochips: proteomic scoring to discriminate cervical cancer from normal cervix," *Cancer Letters*, 211:227-234, 2004.

Woodbury and Vinton., "Methods of screening combinatorial libraries using immobilized or restrained receptors," *J. Chromatogr B Biomed. Sci. Appl.*, 725:113-137, 1999.

Xiao et al., "A preliminary analysis of non-small cell lung cancer biomarkers in serum," *Biomedical and Environmental Sciences*, 16:140-148, 2003.

(56) References Cited

OTHER PUBLICATIONS

Xiao et al., "Discovery of laryngeal carcinoma by serum proteomic pattern analysis," *Science in China Ser. C Life Sciences*, 47:219-223, 2004.
Xie et al., "Biochemical characterization of the TATA-binding Gal4 activation domain complex," *JBC*, 275:31914-31920, 2000.
Xu et al., "Increased incidence of anti-β-amyloid autoantibodies secreted by Epstein-Barr virus transformed B cell lines from patients with Alzheimer's disease," *Mechanisms of Ageing and Development*, 94:213-222, 1997.
Yang et al., "Novel Turns and Helices in Peptides of Chiral alpha-Aminoxy Acids," *J. Amer. Chem. Soc.*, 121:589-590, 1999.
Yang et al., "Protein-peptide interactions analyzed with the two-hybrid system," *Nucl. Acids Res.*, 23:1152-1156, 1995.
Yoo et al., Peptoid architectures elaboration, actuation, and application,: *Curr Opinion Chem Biol*, 12:714-721, 2008.
Zhang et al., "An inhibitor of sequence specific proteolysis that targets the substrate rather than the enzyme," *Chem. Biol.*, 8:391-397, 2001.
Zhang et al., "Genetic selection of short peptides that support protein oligomerization in vivo," *Current Biol.*, 9:417-420, 1999.
Zhang et al., "Selection and practical applications of peptide-binding peptides," *Nature Biotechnol.*, 18:71-74, 2000.
Zhu et al., "A Cdc6-binding peptide selected using a bacterial two-hybrid-like system is a cell cycle inhibitor," *J. Biol. Chem.*, 275:32098-32105, 2000.
Zuckermann, et al., "Discovery of nanomolar ligands for 7-transmembrane G-protein-coupled receptors from a diverse N-(substituted)glycine peptoid library," *J. Med. Chem.*, 37:2678-85, 1994.
Banerjee, et al., "Efficacy of selected natural products as therapeutic agents against cancer," *J. Natural Prod.*, 71:492-6, 2008.
Chhabra et al., "An appraisal of new variants of Dde amine protecting group for solid phase peptide synthesis," *Tetrahedron Lett.*, 39:1603-6, 1998.
Fields and Song, "A novel genetic system to detect protein-protein interactions," *Nature*, 340:243-246, 1989.
Fouladi, "Histone deacetylase inhibitors in cancer therapy," *Cancer Invest.*, 24:521-7, 2006.
Hamada and Shioiri, "Recent progess of the synthetic studies of biologically active marine cyclic peptides and depsipeptides," *Chem. Rev.*, 105:4441-82, 2005.
Ho, et al., "The mechanism of action of cyclosporin A and FK506," *Clin. Immunol. Immunopathol.*, 80:S40-5, 1996.
Joo, et al., "High-throughput sequence determination of cyclic peptide library members by partial Edman degradation/mass spectrometry," *J. Amer. Chem. Soc.*, 128:13000-9, 2006.
Lech-Maranda, et al., "Depsipeptide (FK228) as a novel histone deacetylase inhibitor: mechanism of action and anticancer activity," *Mini Rev. Med. Chem.*, 7:1062-9, 2007.
Lim, et al., "Identification of a peptoid inhibitor of the proteasome 19S regulatory particle," *J. Amer. Chem. Soc.*, 129:7750-1, 2007.
Liu, et al., "Novel peptide-based encoding system for "one-bead one-compound" peptidomimetic and small molecule combinatorial libraries," *J. Amer. Chem. Soc.*, 124:7678-80, 2002.
Rezai, et al., "Conformational flexibility, internal hydrogen bonding, and passive membrane permeability: successful in silico prediction of the relative permeabilities of cyclic peptides," *J. Amer. Chem. Soc.*, 128:14073-80, 2006.
Rezai, et al., "Testing the conformational hypothesis of passive membrane permeability using synthetic cyclic peptide diastereomers," *J. Amer. Chem. Soc.*, 128:2510-1, 2006.
Satoh, et al., "Synthetic peptides derived from the fourth domain of CD4 antagonize off function and inhibit T cell activation," *Biochem. Biophys. Res. Commun.*, 224:433-43, 1996.
Shin, et al., "Cyclic peptoids," *J. Amer. Chem. Soc.*, 129:3218-25, 2007.
Udugamasooriya and Spaller, "Conformatinal constraint in protein ligand design and the inconsistency of binding entropy," *Biopolymers*, 89:653-67, 2008.
Uttamchandani, et al., "Small molcule microarrays recent advances and applications," *Curr. Opin. Chem. Biol.*, 9:4-13, 2005.
Xiao, et al., "Design and synthesis of a cell-permeable synthetic transcription factor mimic," *J. Comb. Chem.*, 9:592-600, 2007.
Zuckerman et al., "Efficient method for the preparation of peptoids [oligo(N-substituted glycines)] by submonomer solid-phase synthesis," *J. Am. Chem. Soc.*, 114:10646-10647, 1992.

1: Glu-Nmea-Npip-Nall-Nphe-Nall-Nffa-Nmea
2: Glu-Nall-Nleu-Npip-Nphe-Nleu-Nleu-Nmea
3: Glu-Nffa-Nmea-Nys-Npip-Nall-Nphe-Nmea
4: Glu-Nphe-Nffa-Nleu-Nffa-Npip-Nmea-Nmea
5: Glu-Nall-Nlys-Nffa-Nmea-Nleu-Nphe-Nmea

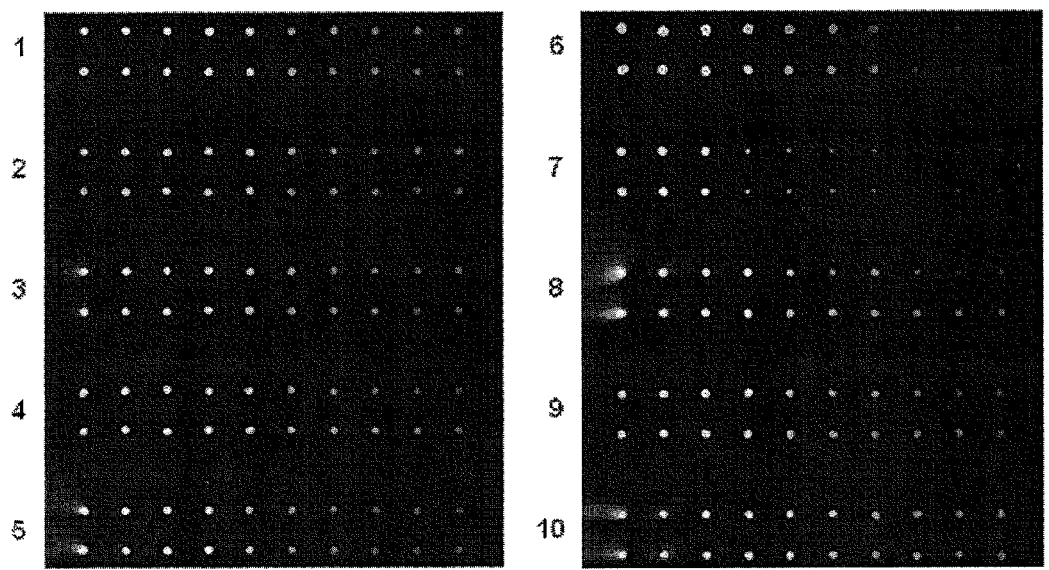

1: β-Ala-Cys-Glu(Biotin)-Glu-Nmea-Npip-Nall-Nphe-Nall-Nffa-Nmea
2: β-Ala-Cys-Glu(Biotin)-Glu-Nall-Nleu-Npip-Nphe-Nleu-Nleu-Nmea
3: β-Ala-Cys-Glu(Biotin)-Glu-Nffa-Nmea-Nlys-Npip-Nall-Nphe-Nmea
4: β-Ala-Cys-Glu(Biotin)-Glu-Nphe-Nffa-Nleu-Nffa-Npip-Nmea-Nmea
5: β-Ala-Cys-Glu(Biotin)-Glu-Nall-Nlys-Nffa-Nmea-Nleu-Nphe-Nmea
6: β-Ala-Cys-Glu(Biotin)-Glu-Nall-Nphe-Nleu-Npip-Nphe-Nffa-Nmea
7: β-Ala-Cys-Glu(Biotin)-Glu-Nleu-Nffa-Nmea-Nall-Npip-Nleu-Nmea
8: β-Ala-Cys-Glu(Biotin)-Glu-Nffa-Nphe-Nall-Nlys-Npip-Nall-Nmea
9: β-Ala-Cys-Glu(Biotin)-Glu-Nphe-Nleu-Npip-Nffa-Nall-Nmea-Nmea
10: β-Ala-Cys-Glu(Biotin)-Glu-Nleu-Nlys-Npip-Nall-Nphe-Nall-Nmea

FIG. 19

COMPOSITIONS AND METHODS FOR PRODUCING CYCLIC PEPTOID LIBRARIES

This invention was made with government support under Grant Number NO1-HV-28185 awarded by the National Institutes of Health. The government has certain rights in the invention.

This application claims priority to U.S. Provisional Application Ser. No. 61/252,333 filed Oct. 16, 2009, which is incorporated herein by reference in its entirety.

BACKGROUND OF THE INVENTION

I. Field of the Invention

Embodiments of this invention are directed generally to biology, medicine, drug discovery, and diagnostics. In particular embodiments the present invention is directed to cyclic peptoid arrays and use thereof.

II. Background

Peptoid (N-substituted oligoglycines) libraries are rich sources of protein ligands. However, the hits that one obtains from library screening experiments against a given protein generally have only a modest affinity for the target (usually low µM $K_D$s). Therefore, it would be desirable to develop peptoid or libraries that provide hits with higher affinity as a starting point for drug development. It seems likely that one reason for the modest affinity of the hits is that peptoids are inherently "floppy" molecules. Assuming that much of the peptoid molecule must "lock in" to a particular conformation upon binding the protein target, this means that the entropic cost of binding will be high, thus limiting the binding affinity. In theory, peptoids or peptoid-like molecules that are stiffer and might closely resemble the bound conformation even in the unbound state would bind with higher affinity.

One way to attempt to limit the conformational flexibility of a peptoid chain would be to cyclize it. By tethering the two ends of the molecule, many conformations available to the linear molecule can no longer be achieved.

Drug-like small molecules (<500 Daltons) generally do not bind well to the relatively shallow surfaces of proteins involved in protein-protein interactions. Thus, in order to develop effective therapeutic agents against these increasingly important targets, it is necessary to develop libraries of compounds able to cover a greater surface area and engage in multiple contacts with the target protein, as well as efficient methods to screen these libraries. With regard to their protein-binding properties, peptides are an attractive class of molecules, but linear peptides have many undesirable features. They are peptidase- and protease-sensitive, relatively cell impermeable and generally form complexes with only modest dissociation constants in the high nM to mid µM range. However, cyclic peptides can exhibit enhanced cell permeability (Rexai et al., 2006a; Rezai et al., 2006b) and are much less sensitive to enzymatic degradation (Satoh et al., 1996). Moreover, it is presumed that the conformational restriction imposed by cyclization may generally afford higher binding affinities, though rigorous proof for this idea is lacking (Udugamasooriya and Spaller, 2008; Martin, 2007). Indeed, many naturally occurring cyclic peptides and depsipeptides have been found to display potent biological activities (Ho et al., 1996; Banerjee et al., 2008; Lech-Maranda et al., 2007; Fouladi, 2006; Hamada and Shioiri, 2005). This interest has led to the development of facile methods for the creation of either synthetic (Joo et al., 2006) or genetically encoded (Scott et al., 1999; Venkatesh et al., 2000) libraries of cyclic peptides as potential sources of drug leads.

A limitation of peptide libraries, cyclic or linear, is that only a relatively small number of building blocks are available. Moreover, although cyclic peptides can be more cell permeable than their linear counterparts, this appears to be dependent on their ability to form intramolecular hydrogen bonds (Rezai et al., 2006b), a property that is likely to vary from compound to compound. Therefore, the inventors became interested in the development of libraries of cyclic peptoids (N-substituted oligoglycines) (Simon et al., 1992; Shin et al., 2007) as potential protein ligands. Large libraries of peptoids with a wide variety of different side chains (Figliozzi et al., 1996; Horn et al., 2004; Alluri et al., 2003) are readily accessible using split and pool methods and efficient protocols with which to screen these libraries for protein binding have been developed (Alluri et al., 2003; Alluri et al., 2006; Xiao et al., 2007; Reddy et al., 2004; Lim et al., 2007; Zuckermann et al., 1994; Udugamasooriya et al., 2008). However, additional methods of producing coded cyclic peptoid arrays and identifying and sequencing cyclic peptoids is needed.

SUMMARY OF THE INVENTION

A central problem with the use of libraries of cyclic peptides, peptoids and the like is that they are difficult to characterize after screening. In a one-bead-one-compound library created by split and pool synthesis, one does not know the identity of the molecule on each bead a priori. It must be determined post-screening. Given the limited amount of compound present on each bead, this must be done by tandem mass spectrometry. In this technique the molecular ion is isolated, then fragmented in the instrument to provide sequence information. The major site of fragmentation is at the amide bonds linking the monomers of the peptoid. When linear molecules fragment, they provide shorter fragments. The loss of mass in each fragment relative to the molecular ion provides sequence information. However, cyclic molecules can fragment at any of the amide bonds and simply produce a linear molecule, not fragments. This makes sequencing cyclic molecules by mass spectrometry extremely difficult. The present invention overcomes this problem by including, on a single bead in a plurality of single beads in a library, both a linear and cyclic peptoid wherein the linear peptoid is homologous to the cyclic peptoid and which can be utilized to identify the sequence of a high affinity cyclic peptoid after a biological sample is screened against a cyclic peptoid microarray.

Single beads from the library can be separated into the individual wells of microtiter plates and the molecules can be cleaved form the resin with mild acid. This releases both the linear and cyclic molecules into solution. A robotic spotter is then employed to spot each solution on activated glass microscope slides. While both the linear and cyclic molecules are spotted onto the slides, only the cyclic molecule contains an attachment residue (e.g., a cysteine thiol or other reactive group) and thus can attach covalently to an activated substrate (e.g., maleimide-activated surface or other activated surface). The linear molecule is washed off of the slide in the post-spotting wash. A sufficient volume of solution left in each well of the microtiter plates so that once a peptoid is deemed interesting in a screening experiment one can go to the appropriate well of the plate and use tandem mass spectrometry to sequence the linear molecule present in the solution. An effective encoding strategy for cyclic peptoid libraries is developed based on co-synthesis of linear and cyclic peptoids. This method, because of the incorporation of an attachment residue solely in the cyclic molecule, is particularly useful for the creation of cyclic peptoid microarrays.

Embodiments of the invention include methods of producing a cyclic peptoid/linear peptoid pair comprising: (a) independently coupling an array attachment residue (that is a residue having a chemical group that interacts with a functionalized array substrate and immobilizes peptoid compositions containing the attachment residue to the array substrate) and a first peptoid initiator residue to an external surface of a substrate; (b) coupling a second peptoid initiator residue to the array attachment residue; (c) coupling a cyclizing residue to the second peptoid initiator residue; (d) synthesizing concurrently a first peptoid coupled to the first initiator residue and a second peptoid coupled to the cyclizing residue, wherein the first and second peptoid comprise the same sequence of residues; and (e) cyclizing the second peptoid coupled to the cyclizing residue.

A "peptoid initiator residue" can be any peptoid or chemical moiety to which a peptoid can be synthesized, extended, or polymerized.

A "cyclizing residue" is a residue containing a side chain having a chemical group that reacts with the terminal residue of a peptoid forming a cyclic peptoid. For example, the cyclizing residue can comprise a —COOH group or activated carbonyl group (COR) wherein R is a leaving group that reacts with the terminal amine of the terminal peptoid residue (to form a cyclic peptoid. The peptoid chain having the cyclizing residue and the reactive terminal peptoid residue can be considered to be, before cyclization, a "cyclic peptoid intermediate."

In certain aspects, the support is a peptoid-primed support, e.g., a beta-alanine primed support. The support can be a bead or any other surface on which a peptoid can be synthesized or polymerized. In particular aspects, the bead is a Rink-amide bead. In certain aspects, an attachment residue contains a thiol or a furan group and which can react with a functional group or reactive moiety on an activated or functioralized array substrate. In certain aspects, the cyclizing residue side chain comprises a COOH group. In a further aspect, the cyclizing residue is an amino acid residue having a carboxylic acid side chain including, but not limited to, a glutamic acid or aspartic acid residue or a peptoid having a carboxylic acid side chain off the amino group of the peptoid. The methods can further comprise, prior to step (e), terminating the first and second peptoids with a peptoid group that can be coupled to the side chain of the cyclizing residue to form a cyclic peptoid. The terminal peptoid residue can be, but is not limited to a Nmea, Napp, Nleu, Nch, or Nmpa residue.

The method can further comprise cleaving the cyclic peptoid from the substrate and immobilizing a plurality of cleaved cyclic peptoids on an array substrate. The plurality of cyclic peptoids on an array can be contacted with a sample or with a binding target and a cyclic peptoid the binds a component of the sample or the binding target can be identified. The method can comprise sequencing a corresponding linear peptoid co-synthesized with a cyclic peptoid of interest to determine the sequence of the cyclic peptoid that binds the binding target. The present invention includes both a high affinity cyclic peptoid ligand and the corresponding linear ligand, the latter of which is useful to identify the sequence of the cyclic peptoid ligand and may also be useful as a ligand having low to moderate or high affinity to a binding target(s). The linear ligand identified herein may also be dimerized to form a peptoid dimer.

Certain embodiments include peptoid compositions having the formula N—(C)n-X—B—X—Z-(L)m-Y—(C)n-N; wherein B is a bead support; (C) is a peptoid monomer; n is 4, 5, 6, 7 to 6, 7, 8, 9, 10; X is a coupling residue that couples the peptoid to the external surface of the bead support; Z is an array attachment residue; L is a linker residue that couples Z and Y; m is 0 to 10; N is an N-terminal peptoid residue; and Y is a cyclizing residue that reacts with N cyclizing peptoid (C)n. In certain aspects, B is a Rink-amide bead. Component X can be any moiety from which a peptoid can be synthesized or polymerized, for example any peptoid residue such as a β-alanine residue. Component Z is an attachment residue that comprises a side chain having a functional group that is compatible with and will couple to the functional groups of a functionalized or activated array substrate. Component Y is a cyclizing residue that has a side chain that can be coupled with the terminal peptoid residue to form a cyclic peptoid. Component Y can be selected from amino acid monomers or peptoid monomers having a reactive side chain. The side chain can comprise a COR group wherein R is selected from hydroxyl group, alkoxy, aryloxy, halogen (e.g., a COOH group) and includes, but is not limited to, glutamyl and aspartyl side chains. Component N is the terminal peptoid residue that can be reacted with the side chain of the cyclizing residue to form a cyclic peptoid. N can be, but is not limited to a Nmea, Napp, Nleu, Nch, or Nmpa residue.

Still further embodiments include cyclic peptoid compositions having the formula: N—(C)n-X—B—X—Z-(L)m-Y—(C)n-N; wherein B is a bead support; (C) is a peptoid monomer; n is 4, 5, 6, 7 to 6, 7, 8, 9, 10; X is a coupling residue that couples the peptoid to the external surface of the bead support; Z is an array attachment residue; L is a linker residue that couples Z and Y; m is 0 to 10; N is an N-terminal peptoid residue; and Y is a cyclizing residue that is chemically coupled to N, cyclizing peptoid (C)n. In certain aspects, B is a Rink-amide bead. Component X can be any moiety from which a peptoid can be synthesized or polymerized, for example any peptoid residue such as a β-alanine residue. Component Z is an attachment residue that comprises a side chain having a functional group that is compatible with and will couple to the functional groups of a functionalized or activated array substrate. Component Y is a cyclizing residue that has a side chain that can be coupled with the terminal peptoid residue to form a cyclic peptoid. The side chain can comprise a —COOH group and includes glutamyl and aspartyl side chains. Component N is the terminal peptoid residue that can be reacted with the side chain of the cyclizing residue to form a cyclic peptoid. N can be, but is not limited to a Nmea, Napp, Nleu, Nch, or Nmpa residue.

Certain embodiments include peptoid compositions having the formula: Z-(L)m-Y—(C)n-N; wherein (C) is a peptoid monomer; n is 4, 5, 6, 7, to 6, 7, 8, 9, 10; Z is an array attachment residue; L is a linker; m is 0-10; N is a terminal peptoid residue; and Y is a cyclizing residue having a chemical group that cyclizes with N. In certain aspects B is a Rink-amide bead. Component X can be any moiety from which a peptoid can be synthesized or polymerized, for example any peptoid residue such as a β-alanine, residue. Component Z is an attachment residue that comprises a side chain having a functional group that is compatible with and will couple to the functional groups of a functionalized or activated array substrate. Component Y may be further defined as a cyclizing residue that has a side chain that can be coupled with the terminal peptoid residue to form a cyclic peptoid. The side chain of a cyclizing residue can comprise a COOH group and includes glutamyl and aspartyl side chains. Component N is the terminal peptoid residue that can be reacted with the side chain of the cyclizing residue to form a cyclic peptoid. N can be, but is not limited to a Nmea, Napp, Nleu, Nch, or Nmpa residue.

Embodiments also include cyclic peptoid microarrays comprising (a) a support; and (b) a cyclic peptoid bound to the support wherein the cyclic peptoid comprises a compound of the formula Z—Y—(C)n-N wherein (C) is a peptoid monomer; n is 4, 5, 6, 7, to 6, 7, 8, 9, 10; N is a terminal peptoid residue; Y is a cyclizing residue chemically coupled to N. Component Z is an attachment residue that comprises a side chain having a functional group that is compatible with and will couple to the functional groups of a functionalized or activated array substrate. Component Y is a cyclizing residue that has a side chain that can be coupled with the terminal peptoid residue to form a cyclic peptoid. The side chain can comprise a —COOH group and includes glutamyl and aspartyl side chains. Component N is the terminal peptoid residue that can be reacted with the side chain of the cyclizing residue to a cyclic peptoid. N can be, but is not limited to a Nmea, Napp, Nleu, Nch, or Nmpa residue.

Another embodiment comprises methods of producing a cyclic peptoid composition comprising (a) coupling an array attachment residue to an external surface of a substrate; (b) coupling a cyclizing residue to the array attachment residue; (c) coupling a peptoid initiator residue to the cyclizing residue; (d) synthesizing a peptoid coupled to the peptoid initiator; and (e) cyclizing the peptoid coupled to the cyclizing residue. The support can be a Rink-amide bead.

A further embodiment comprises cyclic peptoid arrays produced by (a) synthesizing a cyclic peptoid/linear peptoid pair by (i) coupling an array attachment residue (Z) and a first peptoid initiator residue to a substrate; (ii) coupling a cyclizing residue (Y) to the array attachment residue; (iii) coupling a second peptoid initiator residue to the cyclizing residue; (iv) synthesizing concurrently a first peptoid coupled to the first initiator residue and a second peptoid coupled to the second initiator residue, wherein the first and second peptoid comprise the same sequence of residues; and (v) cyclizing the second peptoid coupled to the cyclizing residue; (b) removing the cyclic peptoid from the substrate; (c) immobilizing a portion of the cyclic peptoid onto an array substrate.

Other embodiments include methods of profiling a plurality of distinct ligand binding moieties in a sample comprising (a) providing an array of cyclic peptoids having a plurality of random structures; (b) contacting said array with a biological sample comprising a ligand binding moiety; and (c) assessing binding of the ligand binding moiety to said array, wherein binding of the ligand binding moiety to said array detects the ligand binding moiety in said sample.

Embodiments also include methods of identifying a cyclic peptoid ligand comprising (a) providing an array of cyclic peptoids having a plurality of random structures; (b) contacting said array with a target; and (c) assessing binding of the target to said array, wherein binding of the target to said array detects a cyclic peptoid ligand that binds the target. The method further comprising obtaining a peptoid sequence of the cyclic peptoid ligand, wherein obtaining the sequence of the cyclic peptoid ligand comprises sequencing a linear peptoid having a peptoid sequence identical to the cyclic peptoid ligand.

Other embodiments include methods of screening a cyclic peptoid ligand for binding specificity comprising (a) providing a cyclic peptoid ligand and a corresponding linear peptoid; (b) providing a plurality of cell types, the plurality of cell types being distinguished on the basis of a cell surface structure, wherein the plurality of cell types are differentially labeled to distinguish each cell type; (c) contacting the cyclic peptoid ligand with the plurality of cell types; (d) determining which of the plurality of cell types the cyclic peptoid ligand binds; and (e) sequencing the corresponding linear peptoid to determine the sequence of the cyclic peptoid ligand.

Certain advantages of certain embodiments of the invention include, but are not limited to the following: synthesis of both linear and cyclic molecules on external sites on a bead, rather than being forced to differentially synthesize a linear molecule on the inside of the bead and a cyclic molecule on the outside of the bead; also, the incorporation of an attachment residue into the cyclic molecule, but not the linear molecule, insures that when the mixture of the two is spotted onto a maleimide-activated slide, only the cyclic molecule will be attached.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 3A) General structure of the cyclic and linear molecules made on each bead before cleavage and deprotection of the thiol side chain. Below: Sequences of the variable regions of five peptoids picked for the spotting experiment. (FIG. 3B) Fluorescent image of microarrays in which each of the five peptoids have been spotted onto the activated surface. A DMSO solution of each peptoid ($\approx$2 mM) was spotted two times, the solution was diluted three-fold, spotted again, etc. After washing and drying, the arrays were hybridized with Cy3-conjugated streptavidin, washed and the slide was scanned with a fluorescence scanner (see ref. 30 for details). The spots are false-colored green. (FIG. 3C) The Cys is essential for retention of the peptoid on the microarray. Two peptoids were synthesized. Each had the sequence Fluorescein-Nlys-Nser-Nleu-Nser-Nall-Npip-Nlys-Nlys. One peptoid also contained a C-terminal cysteine, while the other did not. The two peptoids were spotted onto a maleimide-activated glass slide. After washing, the slide was scanned using a fluorescence scanner. The fluorescence intensity is false-colored blue.

FIG. 19—Hybridization of biotin-labeled cyclic peptoids microarray and Streptavidin-Cy3. Microarrays consisting of biotin-labeled cyclic peptoids with Nmea at the N-terminal were prepared. Biotin-labeled cyclic peptoids were spotted onto maleimide-functionalized glass slides with 3-fold serial dilution of about 2 mM solution. Microarrays were equilibrated with 1×TBST (50 mM Tris/150 mM NaCl/0.1% Tween 20, pH 8.0) for 30 min at 4° C. Microarray slides were incubated with Streptavidin-Cy3 (10 µL, Sigma) and BSA (50 µL of 2 mg/mL) in 1×TBST (total 1 mL solution) with gentle shaking for 45 min at 4° C. The slides were washed with 1×TBST (3×5 min) at 4° C., and then dried by centrifugation. Hybridized microarrays were scanned with a GenePix 4000B scanner.

DETAILED DESCRIPTION OF THE INVENTION

Figure 1:
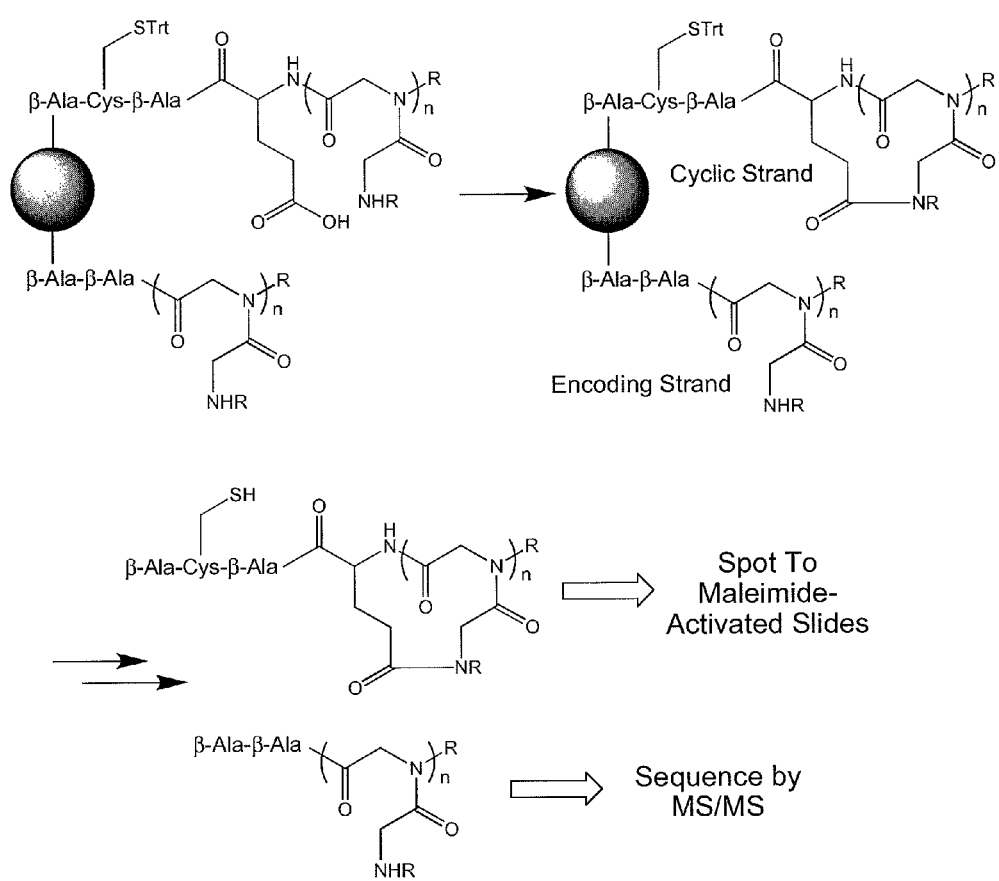
FIG. 1—Schematic view of the general strategy employed to create a library in which each bead carries a cyclic peptoid and an analogous linear encoding strand. Only the cyclic molecule contains a thiol and thus will couple to a maleimide-activated glass slide.

Embodiments of the invention include methods and compositions for encoding a cyclic molecule on a bead with a corresponding linear species as well as methods for using the same. The amount of linear molecule relative to cyclic molecule should be minimalized during screening. In addressing a similar issue, Pei and co-workers used a bead and solvents of different polarities to synthesize a cyclic molecule on the exterior of a bead and synthesize a corresponding linear molecule in interior of the same bead (JACS (2006) 128, 13000). This strategy maintains a physical link between the cyclic and linear molecules, thus providing a viable encoding strategy in which once a cyclic peptoid was identified the corresponding linear molecule could be sequenced. However, the Pei strategy requires extensive manipulations during library synthesis in which solvents have to be changed at each step with the cyclic and linear molecule being synthesized by essentially two separate reaction schemes.

The inventors have developed a strategy that can be used to synthesize the cyclic molecule/linear molecule pair simultaneously on an external surface of a substrate. Moreover, the methods described are suited for creation of cyclic peptoid libraries for display on microarrays. These arrays are useful for the discovery of peptoids that bind to disease-specific antibodies, as well as other purposes. The methods generally involve treating peptoid-primed Rink amide bead with a solution comprising an attachment residue (e.g., Fmoc-protected Cys) and an initiator peptoid residue (e.g., an ivDde-protected beta-alanine residue). The protective groups protect the amines of the residues and can be removed allowing co-synthesis of a cyclic and a linear molecule. The attachment residue provides a reactive group that can be coupled with a functionalized or activated array substrate (e.g., a thiol group of a cysteine) that is used in later steps to affix or immobilize the molecule to an array substrate (e.g., a maleimide-activated microscope slide). Therefore, to create an array of purely cyclic molecules, with little or no linear compound—only cyclized peptoids contain an attachment residue.

In order to cyclize the peptoid a cyclizing residue will comprise a side chain that can be coupled with a terminal peptoid residue forming a cyclic peptoid (e.g., a glutamic acid or an aspartic acid). The corresponding linear peptoid chain does not have a cyclizing residue. Following removal of protective groups both chains serve as sites for synthesis or polymerization of peptoid chains. These methods eliminate the need to carry out two synthetic operations at each step of library construction, as is necessary in the Pei procedure. Once the linear peptoids are synthesized the bead(s) are exposed to conditions that promote coupling of the side chain group of the cyclizing residue with the N-terminal nitrogen of the peptoid library. Since the linear peptoid chain lacks the cyclizing residue it does not cyclize.

One aspect of the invention is the ability to determine the sequence of hits after screening a one-bead-one-compound library. Since cyclic peptides or peptoids lack a free N-terminus, Edman sequencing cannot be employed. Moreover, while peptoids, like peptides, can be sequenced by tandem mass spectrometry (Paulick et al., 2006), cyclic molecules will fragment at multiple positions, complicating interpretation of the MS/MS spectrum severely. This issue has limited the development of synthetic cyclic peptide libraries. Pei and co-workers addressed this problem recently by developing a "two-compound-one-bead" approach in which each bead contains both a linear and cyclic molecule containing the same peptide sequence (Joo et al., 2006). In other words, the linear molecule encodes the cyclic molecule. This was accomplished using the strategy of Lam (Liu et al., 2002) in which different solvents were employed to segregate beads into two different domains (internal and surface-exposed) to which were attached glutamic acid residues with differentially protected carboxylate side chains. The same peptide chain was then extended from both the internal and external Glu residues. Finally, only the surface-exposed Glu side chains were deprotected, allowing them to be cyclized with the terminal amino group of the peptide. The peptides in the internal layer remained linear and thus served as the encoding strand.

Embodiments of the current invention are directed to a distinct one-bead-two-compound strategy that is tailored to the creation of microarrays, a useful platform for protein fingerprinting and library screening (MacBeath et al., 1999; Uttamchandani et al., 2005). The methods employ differential deprotection to create two chains, both of which contain the peptoid of interest, but only one of which contains both a cyclizing residue to support cyclization as well as an attachment residue to allow specific conjugation of only the cyclic peptoid molecule to an activated or functionalized substrate (Reddy and Kodadek, 2005) (FIG. 1). The linear molecule would not couple to the substrate, but would be present to support tandem MS-based sequencing.

I. CYCLIC PEPTOID LIBRARIES AND ARRAYS

In one example, a 7:1 ratio of Fmoc-Cys(Trt)-OH and ivDde-β-Ala-OH was added to β-Ala-primed Rink amide resin. This ratio was optimized empirically to provide enough linear peptoid for tandem MS sequencing from a single bead, but also produce as much cyclic peptoid as possible. After selective deprotection of Fmoc, Fmoc-β-Ala-OH was again attached to Cys followed, after removal of this Fmoc, by addition of Fmoc-Glu(O-2-PhiPr)—OH. At this point, both the Fmoc and ivDde protecting groups were removed and peptoid synthesis was carried out on both strands. Peptoid residues such as methylamine (Nala), allylamine (Nall), isobutylamine (Nleu), 2-methoxyethylamine (Nmea), ethanolamine (Nhse), piperonylamine (Npip), fufurylamine (Nffa), benzylamine (Nphe), and 1,4-diaminobutane (Nlys) were incorporated using conventional sub-monomer chemistry. Peptoids can be synthesized using a microwave (1000 W) assisted synthesis protocol. Beads can be distributed equally into peptoid synthesis reaction vessels, swelled in dimethylformamide (DMF) and each reaction vessel treated with 2M Bromoacetic acid and 3.2 M Di-isopropylcarbodiimide (DIC). Coupling can be performed in a microwave oven. After washing the beads with DMF, each vessel can be treated with a distinct primary amine that can be coupled in a microwave. Beads can be washed, pooled, randomized and redistributed equally into peptide synthesis vessels, and the procedure can be repeated until the desired length is achieved.

The 2-PhiPr protecting group on the Glu side chain is then removed selectively with 1% TFA. Finally, macrocyclization is carried out using the method of Kirshenbaum and colleagues (PyBOP (3 eq.), HOBt (3 eq.) and DIPEA (10 eq.) (Shin et al., 2007). Note that the linear molecule lacks two residues present in the cyclic molecule and thus the mass peaks derived from each can be distinguished easily, facilitating analysis and sequence determination.

To determine the efficacy of this procedure, individual beads were separated and treated with acid to cleave the molecules from the beads, followed by HPLC, MS and MS/MS analysis. The inventors found that in almost every case the sequence of the peptoid on a particular bead could be determined easily by tandem MS analysis of the linear molecule. For some of the molecules, mass spectrometry and HPLC analysis showed that cyclization of the Cys-Glu-containing molecule was clearly incomplete, as linear starting material was clearly detectable. This was not surprising, since a general problem in the creation of cyclic libraries is that not all sequences cyclize with equivalent efficiencies (Li et al., 2005). One would presume that the nature of the N-terminal residue would have the largest effect on cyclization. Indeed, an analysis of more than 50 peptoids by MS/MS revealed that if the N-terminal residue was Nmea, the cyclization yield was almost quantitative. Therefore, one of the preferred terminal residues is Nmea.

Numerous cyclic peptoids can be made in which modest alterations in the side chains of the residues can be introduced in an effort to improve the "fit" of this region of the cyclic peptoid with the binding target. Variants of cyclic peptoids can be assessed for activity in an in vivo assay or in vitro assay against a disease or a condition.

It is contemplated in the present invention that variants or analogs of cyclic peptoids also can be used. Sequence variants can be generated by making conservative substitutions in an identified cyclic peptoid. Substitutional variants typically contain the exchange of one peptoid residue for another at one or more sites within the molecule, and may be designed to modulate one or more properties of the molecule, in particular the affinity of the molecule for the target, without the loss of other functions or properties.

Peptoids may employ modified, non-natural and/or unusual amino acids. Chemical synthesis may be employed to incorporate such residues into compounds of interest. Non-natural residues include, but are not limited to Aad (2-Aminoadipic acid), EtAsn (N-Ethylasparagine), Baad (3-Aminoadipic acid), Hyl (Hydroxylysine), Bala (beta-alanine), Ahyl (allo-Hydroxylysine propionic acid), Abu (2-Aminobutyric acid), 3Hyp (3-Hydroxyproline), 4Abu (4-Aminobutyric acid), 4Hyp (4-Hydroxyproline piperidinic acid), Acp (6-Aminocaproic acid), Ide (Isodesmosine), Ahe (2-Aminoheptanoic acid), Aile (allo-Isoleucine), Aib (2-Aminoisobutyric acid), MeGly (N-Methylglycine), Baib (3-Aminoisobutyric acid), MeIle (N-Methylisoleucine), Apm (2-Aminopimelic acid), MeLys (6-N-Methyllysine), Dbu (2,4-Diaminobutyric acid), MeVal (N-Methylvaline), Des (Desmosine), Nva (Norvaline), Dpm (2,2'-Diaminopimelic acid), Nle (Norleucine), Dpr (2,3-Diaminopropionic acid), Orn (Ornithine), and EtGly (N-Ethylglycine).

In addition to the variants discussed above, the present inventors also contemplate that structurally similar compounds may be formulated to mimic the key portions of peptoids of the present invention. Such peptoid compounds may be used in the same manner as peptides and can be functional equivalents thereof. Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions. In one aspect a peptoid is thus designed to permit molecular interactions similar to a natural molecule.

The term "attach" or "attached" as used herein, refers to connecting or uniting by a bond, link, force or tie in order to keep two or more components together, which encompasses either direct or indirect attachment such that for example where a first molecule is directly bound to a second molecule or material, and the embodiments wherein one or more intermediate molecules are disposed between the first molecule and the second molecule or material.

A "protecting group" is a moiety which is bound to a molecule and designed to block one reactive site in a molecule, but may be spatially removed upon selective exposure to an activator or a deprotecting reagent. Several examples of protecting groups are known in the literature. The proper selection of protecting group (also known as protective group) for a particular synthesis would be governed by the overall methods employed in the synthesis. Activators include, for example, electromagnetic radiation, ion beams, electric fields, magnetic fields, electron beams, x-ray, and the like. A deprotecting reagent could include, for example, an acid, a base or a free radical. Protective groups are materials that bind to a monomer, a linker molecule or a pre-formed molecule to protect a reactive functionality on the monomer, linker molecule or pre-formed molecule, which may be removed upon selective exposure to an activator, such as an electrochemically generated reagent. Protective groups that may be used in accordance with an embodiment of the invention preferably include all acid and base labile protecting groups. For example, amine groups can be protected by t-butyloxycarbonyl (BOC) or benzyloxycarbonyl (CBZ), both of which are acid labile, or by 9-fluorenylmethoxycarbonyl (FMOC), which is base labile. Additionally, hydroxyl groups on phosphoramidites may be protected by dimethoxytrityl (DMT), which is acid labile.

Any unreacted deprotected chemical functional groups may be capped at any point during a synthesis reaction to avoid or to prevent further bonding at such molecule. Capping groups "cap" deprotected functional groups by, for example, binding with the unreacted amino functions to form amides. Capping agents suitable for use in an embodiment of the invention include: acetic anhydride, n-acetylimidizole, isopropenyl formate, fluorescamine, 3-nitrophthalic anhydride and 3-sulfoproponic anhydride.

Additional protecting groups that may be used in accordance with an embodiment of the invention include acid labile groups for protecting amino moieties: tertbutyloxycarbonyl,-tert-amyloxycarbonyl, adamantyloxycarbonyl, 1-methylcyclobutyloxycarbonyl, 2-(p-biphenyl)propyl(2)oxycarbonyl, 2-(p-phenylazophenyl)propyl(2)oxycarbonyl, alpha, alpha-dimethyl-3,5-dimethyloxybenzyloxy-carbonyl, 2-phenylpropyl(2)oxycarbonyl, 4-methyloxybenzyloxycarbonyl, benzyloxycarbonyl, furfuryloxycarbonyl, triphenylmethyl (trityl), p-toluenesulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9-fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio)carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2-aminothiophenol); acid labile groups for protecting carboxylic acids: tert-butyl ester; acid labile groups for protecting hydroxyl groups: dimethyltrityl; and basic labile groups for protecting phosphotriester groups: cyanoethyl.

A. Purification of Peptoids

It may be desirable to purify peptoids. Purification techniques are well known to those of skill in the art. These techniques typically involve chromatographic and electrophoretic techniques to achieve partial or complete purification (or purification to homogeneity). Analytical methods particularly suited to the preparation of a pure peptoid are ion-exchange chromatography, exclusion chromatography; polyacrylamide gel electrophoresis; isoelectric focusing. A particularly efficient method of purifying peptoids is fast protein liquid chromatography or even HPLC.

Certain aspects of the present invention concern the purification, and in particular embodiments, the substantial purification, of a peptoid. The term "purified peptoid" as used herein, is intended to refer to a composition, isolatable from other components, wherein the peptoid is purified to any degree relative to its normally-obtainable state. A purified peptoid therefore also refers to a peptoid free from the environment in which it may normally occur.

Generally, "purified" will refer to a peptoid composition that has been subjected to fractionation to remove various other components, and which composition substantially retains its expressed biological activity. Where the term "substantially purified" is used, this designation will refer to a composition in which the peptoid forms the major component of the composition, such as constituting about 50%, about 60%, about 70%, about 80%, about 90%, about 95% or more of the composition by weight.

Various methods for quantifying the degree of purification of the peptoid will be known to those of skill in the art in light of the present disclosure. These include, for example, determining the specific activity of an active fraction, or assessing the amount of peptoid within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the peptoid exhibits a detectable activity.

B. Peptoid Array

The term "substrate," as used herein, indicates a base material on which processing can be conducted to modify or synthesize a molecule on the surface of the base material or a based material upon which an array of molecules are attached to be used in screening methods (array substrate). Exemplary chemical modifications of a substrate include functionalization and/or depositing a peptoid or an initial residue or base of a peptoid on the surface layer of a base material that is capable of chemically coupling to a peptoid of the invention or a initiator of such a peptoid.

Support materials useful in embodiments of the present invention include, for example, silicon, bio-compatible polymers such as, for example poly(methyl methacrylate) (PMMA) and polydimethylsiloxane (PDMS), glass, SiO2 (such as, for example, a thermal oxide silicon wafer such as that used by the semiconductor industry), quartz, silicon nitride, functionalized glass, gold, platinum, and aluminum. Functionalized surfaces include for example, amino-functionalized glass, carboxy functionalized glass, hydroxy functionalized glass, and amide functionalized beads. Additionally, a support may be coated with one or more layers to provide a surface for molecular attachment or functionalization, increased or decreased reactivity, binding detection, or other specialized application. Support materials and or layer(s) may be porous or non-porous. For example, a support may be comprised of porous silicon. Additionally, the support may be a silicon wafer or chip such as those used in the semiconductor device fabrication industry. A person skilled in the art would know how to select an appropriate support material.

The term "functionalization" as used herein relates to modification of a solid substrate to provide a plurality of functional groups on the substrate surface. By a "functionalized surface" as used herein is meant a substrate surface that has been modified so that a plurality of functional groups are present thereon. The term "functional group" as used herein indicates specific groups of atoms within a molecular structure that are responsible for the characteristic chemical reactions of that structure. Exemplary functional groups include, hydrocarbons, groups containing halogen, groups containing oxygen, groups containing nitrogen and groups containing phosphorus and sulfur all identifiable by a skilled person.

The peptoids present on the array may be linked covalently or non-covalently to the array, and can be attached to the array support (e.g., silicon or other relatively flat material) by cleavable linkers. A linker molecule can be a molecule inserted between the support and peptoid that is being synthesized, and a linker molecule may not necessarily convey functionality to the resulting peptide, such as molecular recognition functionality, but instead elongates the distance between the support surface and the peptoid functionality to enhance the exposure of the peptoid functionality on the surface of the support. Preferably a linker should be about 4 to about 40 atoms long. The linker molecules may be, for example, aryl acetylene, ethylene glycol oligomers containing 2-10 monomer units (PEGs), diamines, diacids, amino acids, among others, and combinations thereof. Examples of diamines include ethylene diamine and diamino propane. Alternatively, the linkers may be the same molecule type as that being synthesized, such as peptoids. A person skilled in the art would know how to design appropriate linkers.

The substrate is typically chemically modified to attach one or more functional groups. The term "attach" or "attached" as used herein, refers to connecting or uniting by a bond, link, force or tie in order to keep two or more components together, which encompasses either direct or indirect attachment such that for example where a first compound is directly bound to a second compound or material, and the embodiments wherein one or more intermediate compounds, and in particular molecules, are disposed between the first compound and the second compound or material.

In particular, in polymer arrays selected functional groups that are able to react with a polymer of choice that forms the polymer arrays are attached to the functionalized substrate surface so that they are presented on the surface. The term "present" as used herein with reference to a compound or functional group indicates attachment performed to maintain the chemical reactivity of the compound or functional group as attached. Accordingly, a functional group presented on a surface, is able to perform under the appropriate conditions the one or more chemical reactions that chemically characterize the functional group.

In those embodiments where an array includes two more features immobilized on the same surface of a solid support, the array may be referred to as addressable. An array is "addressable" when it has multiple regions of different moieties (e.g., different peptoids) such that a region (e.g., a "feature" or "spot" of the array) at a particular predetermined location (e.g., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "probe" may be the one which is to be evaluated by the other (thus, either one could be an unknown mixture of analytes, e.g., antibodies, to be evaluated by binding with the other).

In one aspect, the present invention provides methods, referred to herein as "small molecule printing," for the generation of high density arrays and the resulting compositions, wherein the small molecules are attached to a solid support using chemical moieties that interact with chemical groups on an activated substrate.

Certain aspects of the invention include methods in which a collection of cyclic peptoids is "printed" onto a support to generate high density arrays. In general, this method comprises (1) providing a solid support, wherein the solid support is functionalized with a moiety capable of interacting with a desired chemical group of a compound or a collection of compounds, to form array attachment(s); (2) providing one or more solutions of the same or different cyclic peptoids to be attached to the solid support; (3) delivering the one or more solutions of the same or different cyclic peptoids to the solid support; and (4) capturing the cyclic peptoids on the support, whereby an array of compounds is generated.

As one of ordinary skill in the art will realize, although any desired chemical compound capable of forming an attachment with the solid support may be utilized, it is preferred that those peptoids generated from split-and-pool library or parallel syntheses are utilized. As will be appreciated by one of ordinary skill in the art, the use of split-and-pool libraries enables the more efficient generation and screening of compounds. However, peptoid molecules synthesized by parallel synthesis methods and by traditional methods can also be utilized in the compositions and methods of the present invention.

As mentioned above, the use of parallel synthesis methods are also applicable. Parallel synthesis techniques traditionally involve the separate assembly of products in their own reaction vessels. For example, a microtiter plate containing n rows and m columns of tiny wells which are capable of holding a small volume of solvent in which the reaction can occur, can be utilized. Thus, n variants of reactant type A can be reacted with m variants of reactant type B to obtain a library of n×m compounds.

Subsequently, once the desired compounds have been provided using an appropriate method, solutions of the desired compounds are prepared. In a certain aspects, compounds are synthesized on a solid support and the resulting synthesis beads are subsequently distributed into polypropylene microtiter plates at a density of one bead per well. Typically, the attached compounds are then released from their beads and dissolved in a small volume of suitable solvent. In a particular embodiments a high-precision transcription array robot (Schena et al., 1995; Shalon et al., 1996); each of which is incorporated herein by reference) can be used to pick up a small volume of dissolved compound from each well and repetitively deliver appropriate volumes of solution to defined locations on a series of functionalized glass substrates. This results in the formation of microscopic spots of compounds on the array substrate. In addition to a high precision array robot (e.g., OmniGrid® 100 Microarrayer (Genomic Solutions)), other means for delivering the compounds can be used, including, but not limited to, ink jet printers, piezoelectric printers, and small volume pipetting robots.

Each cyclic peptoid can contain a common functional group that mediates attachment to a support surface. It is preferred that the attachment formed is robust, for example covalent ester, thioester, or amide attachments. In addition to the robustness of the linkage, other considerations include the solid support to be utilized and the specific class of compounds to be attached to the support. Supports include, but are not limited to glass slides, polymer supports or other solid-material supports, and flexible membrane supports. Examples of supports suitable for use in embodiments of the invention are described in U.S. Pat. No. 5,617,060 and PCT Publication WO 98/59360, each of which are incorporated by reference.

In another embodiment the compounds are attached by nucleophilic addition of a functional group of the compounds being arrayed to an electrophile such as isocyanate or isothiocyanate. Functional groups found useful in adding to an isocyanate or isothiocyanate include primary alcohols, secondary alcohols, phenols, thiols, anilines, hydroxamic acid, aliphatic amines, primary amides, and sulfonamides. In certain embodiments, the nucleophilic addition reaction is catalyzed by a vapor such as pyridine. Other volatile nucleophilic reagents may also be used. In certain embodiments, the nucleophile includes an amine. In certain embodiments, a heteroaryl reagent is used.

The support can be optionally washed and dried, and may be stored at −20° C. for months prior to screening.

Arrays utilized in this invention may include between about 10, 100, 1,000, 2,000, 3,000, 4,000, 5,000, 6,000, 7,000, 8,000, 9,000, 10,000, 12,500 to 25,000, 50,000, 75,000, to about 100,000 distinct cyclic peptoids, including values and ranges there between.

C. Linkers

The present invention may comprise peptoids joined to various substrates and/or molecules via a linker. Any of a wide variety of linkers may be utilized to effect the joinder of peptoids. Certain linkers will generally be preferred over other linkers, based on differing pharmacologic characteristics and capabilities. In particular, the linkers will be attached at the free —OH group of a peptoid.

Cross-linking reagents are used to form molecular bridges that tie together functional groups of two molecules. Linking/coupling agents used to combine to peptoids or to couple the peptoids to various substrates include linkages such as avidin-biotin, amides, esters, thioesters, ethers, thioethers, phosphoesters, phosphoramides, anhydrides, disulfides, and ionic and hydrophobic interactions.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with a surface or substrate and through a thiol reactive group reacts with a peptoid composition comprising an attachment residue having a thiol group. Numerous types of disulfide-bond containing linkers are known that can be successfully employed in the methods described herein.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent in vivo. The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1988). The use of such cross-linkers is well understood in the art. Another embodiment involves the use of flexible linkers. U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent.

Peptide linkers that include a cleavage site for an enzyme preferentially located or active within a tumor environment also are contemplated. Exemplary forms of such peptide linkers are those that are cleaved by urokinase, plasmin, thrombin, Factor IXa, Factor Xa, or a metallaproteinase, such as collagenase, gelatinase, or stromelysin.

II. DIAGNOSTIC METHODS

Data generated by detection of component(s) in a test sample can be compared to control data to determine if the target(s) in the test sample is normal. Control data refers to data obtained from comparable samples from a normal cell, sample, or person, which or who is known to have defined profile with regard to a sample component or a sample condition. For each component being detected, a control amount of a component from a normal or standardized sample can be determined. Preferably, the control amount of a component is determined based upon a significant number of samples taken from samples such as normal cells or persons so that it reflects variations of the amount of these targets seen in the normal cell or population.

If the test amount of a particular component is significantly increased or decreased compared to the control amount of the component, then this is a positive indication that the test sample has an underlying defect or contains a particular test substance or organism, or is diagnostic of a particular condition or disease. For example, if the test amount of a biological pathway component is increased or decreased by at least 5-fold or greater than 10-fold compared to the control amount, then this is an indication that the test sample is distinct from a standard or control sample or has an alteration in a biological or non-biological system. At least 1, 5, 10% or more of the elements, including all values and ranges there between, on the array may meet the fold threshold.

In certain embodiments, methods for detecting components of a biological pathway, e.g., a signal transduction pathway, can comprise: providing a support comprising a plurality of cyclic peptoids immobilized on a surface of the support, wherein the cyclic peptoids specifically bind to one or more target component(s) of a sample, contacting a sample with a support, and detecting the components of the biological pathway bound to their corresponding capture agents. In some embodiments, data generated from a test sample can be compared to a control to determine if there is any defect in the biological pathway in the test sample. The sample preparation methods is described in U.S. Patent Application 2002/0137106, incorporated herein by reference.

A. Detection Methods

Methods for detecting targets captured or bound on a solid support can generally be divided into photometric methods of detection and non-photometric methods of detection.

Photometric methods of detection include, without limitation, those methods that detect or measure absorbance, fluorescence, refractive index, polarization or light scattering. Methods involving absorbance include measuring light absorbance of an analyte directly (increased absorbance compared to background) or indirectly (measuring decreased absorbance compared to background). Measurement of ultraviolet, visible and infrared light all are known. Methods involving fluorescence also include direct and indirect fluorescent measurement. Methods involving fluorescence include, for example, fluorescent tagging in immunological methods such as ELISA or sandwich assay. Methods involving measuring refractive index include, for example, surface plasmon resonance ("SPR"), grating coupled methods (e.g., sensors uniform grating couplers, wavelength-interrogated optical sensors ("WIOS") and chirped grating couplers), resonant mirror and interferometric techniques. Methods involving measuring polarization include, for example, ellipsometry. Light scattering methods (nephelometry) may also be used.

Non-photometric methods of detection include, without limitation, magnetic resonance imaging, gas phase ion spectrometry, atomic force microscopy and multipolar coupled resonance spectroscopy. Magnetic resonance imaging (MRI) is based on the principles of nuclear magnetic resonance (NMR), a spectroscopic technique used by scientists to obtain microscopic chemical and physical information about molecules. Gas phase ion spectrometers include mass spectrometers, ion mobility spectrometers and total ion current measuring devices.

Mass spectrometers measure a parameter which can be translated into mass-to-charge ratios of ions. Generally ions of interest bear a single charge, and mass-to-charge ratios are often simply referred to as mass. Mass spectrometers include an inlet system, an ionization source, an ion optic assembly, a mass analyzer, and a detector. Several different ionization sources have been used for desorbing and ionizing analytes from the surface of a support or biochip in a mass spectrometer. Such methodologies include laser desorption/ionization (MALDI, SELDI), fast atom bombardment, plasma desorption, and secondary ion mass spectrometers. In such mass spectrometers the inlet system comprises a support interface capable of engaging the support and positioning it in interrogatable relationship with the ionization source and concurrently in communication with the mass spectrometer, e.g., the ion optic assembly, the mass analyzer and the detector. Solid supports for use in bioassays that have a generally planar surface for the capture of targets and adapted for facile use as supports with detection instruments are generally referred to as biochips.

B. Analysis of Data

Data generated by quantitation of the amount of a sample component of interest (target) bound to each peptoid on the array (e.g., signal transduction components, immunological components, plasma membrane enzyme mediators, cell cycle components, developmental cycle components, or pathogen components) can be analyzed using any suitable means. In one embodiment, data is analyzed with the use of a programmable digital computer. The computer program generally contains a readable medium that stores codes. Certain code can be devoted to memory that includes the location of each feature on a support, the identity of the binding elements at that feature and the elution conditions used to wash the support surface. The computer also may contain code that receives as input, data on the strength of the signal at various addressable locations on the support. This data can indicate the number of targets detected, including the strength of the signal generated by each target.

Data analysis can include the steps of determining signal strength (e.g., height of peaks) of a target(s) detected and removing "outliers" (data deviating from a predetermined statistical distribution). The observed peaks can be normalized, a process whereby the height of each peak relative to some reference is calculated. For example, a reference can be background noise generated by instrument and chemicals (e.g., energy absorbing molecule) which is set as zero in the scale. Then the signal strength detected for each target can be displayed in the form of relative intensities in the scale desired. Alternatively, a standard may be admitted with the sample so that a peak from the standard can be used as a reference to calculate relative intensities of the signals observed for each target detected.

Data generated by the detector, e.g., the mass spectrometer, can then be analyzed by computer software. The software can comprise code that converts signal from the detector into computer readable form. The software also can include code that applies an algorithm to the analysis of the signal to determine whether the signal represents a "peak" in the signal corresponding to a target. The software also can include code that executes an algorithm that compares signal from a test sample to a typical signal characteristic of "normal" or standard sample and determines the closeness of fit between the two signals. The software also can include code indicating whether the test sample has a normal profile of the target(s) or if it has an abnormal profile.

C. Conditions or Disease States

A binding profile of one or more sample components (biomarkers) can be used to predict, diagnose, or assess a condition or disease state in a subject from which the sample was obtained. A disease state or condition includes, but is not limited to cancer, autoimmune disease, inflammatory disease, infectious disease, neurodegenerative disease, cardiovascular disease, bacterial infection, viral infection, fungus infection, prion infection, physiologic state, contamination state, or health in general. The methods of the invention can use binding profiles and peptoid ligands to differentiate between different forms of a disease state, including pre-disease states or the severity of a disease state. For example, the methods may be used to determine the metastatic state of a cancer or the susceptibility to an agent or disease state. Embodiments of the invention include methods and compositions for assessing ligand binding moieties present in breast cancer, lung cancer, prostate cancer, cervical cancer, head and neck cancer, testicular cancer, ovarian cancer, skin cancer, brain cancer, pancreatic cancer, liver cancer, stomach cancer, colon cancer, rectal cancer, esophageal cancer, lymphoma, and leukemia.

Further embodiments can be used to assess ligand binding moieties present in autoimmune diseases such as acute disseminated encephalomyelitis (ADEM), acute necrotizing hemorrhagic leukoencephalitis, Addison's disease, agammaglobulinemia, allergic asthma, allergic rhinitis, alopecia greata, amyloidosis, ankylosing spondylitis, anti-GBM/anti- TBM nephritis, antiphospholipid syndrome (APS), autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura (ATP), autoimmune thyroid disease, axonal & neuronal neuropathies, Balo disease, Behcet's disease, bullous pemphigoid, cardiomyopathy, Castlemen disease, celiac sprue (nontropical) Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogan's syndrome, cold agglutinin disease, congenital heart block, coxsackie myocarditis, CREST disease, essential mixed cryoglobulinemia, demyelinating neuropathies, dermatomyositis, Devic's disease (neuromyelitis optica), discoid lupus, Dressler's syndrome, endometriosis, eosinophillic fasciitis, erythema nodosum, experimental allergic encephalomyelitis, Evan's syndrome, fibromyalgia, fibrosing alveolitis, giant cell arteritis (temporal arteritis), glomerulonephritis, Goodpasture's syndrome, Grave's disease, Guillain-Barre syndrome, Hashimoto's encephalitis, Hashimoto's thyroiditis, hemolytic anemia, Henock-Schoniein purpura, herpes gestationis, hypogammaglobulinemia, idiopathic thrombocytopenic purpura (ITP), IgA nephropathy, immunoregulatory lipoproteins, inclusion body myositis, insulin-dependent diabetes (type 1), interstitial cystitis, juvenile arthritis, juvenile diabetes, Kawasaki syndrome, Lambert-Eaton syndrome, leukocytoclastic vasculitis, lichen planus, lichen sclerosus, ligneous conjunctivitis, linear IgA disease (LAD), Lupus (SLE), Lyme disease, Meniere's disease, microscopic polyangitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars plantis (peripheral uveitis), pemphigus, peripheral neuropathy, perivenous encephalomyelitis, pernicious anemia, POEMS syndrome, polyarteritis nodosa, type I, II & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasis, Raynaud's phenomena, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Slogren's syndrome, sperm and testicular autoimmunity, stiff person syndrome, subacute bacterial endocarditis (SBE), sympathetic ophthalmia, Takayasu's arteritis, temporal arteritis/giant cell arteries, thrombocytopenic purpura (TPP), Tolosa-Hunt syndrome, transverse myelitis, ulcerative colitis, undifferentiated connective tissue disease (UCTD), uveitis, vasculitis, vesiculobullous dermatosis, vitiligo or Wegener's granulomatosis or, chronic active hepatitis, primary biliary cirrhosis, cadilated cardiomyopathy, myocarditis, autoimmune polyendocrine syndrome type I (APS-I), cystic fibrosis vasculitides, acquired hypoparathyroidism, coronary artery disease, pemphigus foliaceus, pemphigus vulgaris, Rasmussen encephalitis, autoimmune gastritis, insulin hypoglycemic syndrome (Hirata disease), Type B insulin resistance, acanthosis, systemic lupus erythematosus (SLE), pernicious anemia, treatment-resistant Lyme arthritis, polyneuropathy, demyelinating diseases, atopic dermatitis, autoimmune hypothyroidism, vitiligo, thyroid associated ophthalmopathy, autoimmune coeliac disease, ACTH deficiency, dermatomyositis, Sjögren syndrome, systemic sclerosis, progressive systemic sclerosis, morphea, primary antiphospholipid syndrome, chronic idiopathic urticaria, connective tissue syndromes, necrotizing and crescentic glomerulonephritis (NCGN), systemic vasculitis, Raynaud syndrome, chronic liver disease, visceral leishmaniasis, autoimmune C1 deficiency, membrane proliferative glomerulonephritis (MPGN), prolonged coagulation time, immunodeficiency, atherosclerosis, neuronopathy, paraneoplastic pemphigus, paraneoplastic stiff man syndrome, paraneoplastic encephalomyelitis, subacute autonomic neuropathy, cancer-associated retinopathy, paraneoplastic opsoclonus myoclonus ataxia, lower motor neuron syndrome and Lambert-Eaton myasthenic syndrome.

Yet further embodiments of the invention include methods and compositions for assessing ligand binding moieties present in infectious diseases such as Acquired immunodeficiency syndrome (AIDS), Anthrax, Botulism, Brucellosis, Chancroid, Chlamydial infection, Cholera, Coccidioidomycosis, Cryptosporidiosis, Cyclosporiasis, Diphtheria, Ehrlichiosis, Arboviral Encephalitis, Enterohemorrhagic *Escherichia coli* (*E. coli*), Giardiasis, Gonorrhea, *Haemophilus influenzae*, Hansen's disease (leprosy), Hantavirus pulmonary syndrome, Hemolytic uremic syndrome, Hepatitis A, Hepatitis B, Hepatitis C, Human immunodeficiency virus (HIV), Legionellosis, Listeriosis, Lyme disease, Malaria, Measles, Meningococcal disease, Mumps, Pertussis (whooping cough), Plague, Paralytic Poliomyelitis (polio), Psittacosis (parrot fever), Q Fever, Rabies, Rocky Mountain spotted fever, Rubella, Congenital rubella syndrome, Salmonellosis, Severe acute respiratory syndrome (SARS), Shigellosis, Smallpox, Streptococcal disease (invasive Group A), Streptococcal toxic shock syndrome (STSS), *Streptococcus pneumoniae*, Syphilis, Tetanus, Toxic shock syndrome, Trichinosis, Tuberculosis, Tularemia, Typhoid fever, Vancomycin-Intermediate/Resistant *Staphylococcus aureus, Varicella*, Yellow fever, variant Creutzfeldt-Jakob disease (vCJD), Dengue fever, Ebola hemorrhagic fever, Echinococcosis (Alveolar Hydatid disease), Hendra virus infection, Human monkeypox, Influenza A H5N1 (avian influenza), Lassa fever, Marburg hemorrhagic fever, Nipah virus, O'nyong-nyong fever, Rift Valley fever, Venezuelan equine encephalitis, and West Nile virus (see U.S. Government Accounting Office publication GAO-04-877 "Disease Surveillance").

In still yet further embodiments, the invention include methods and compositions for assessing ligand binding moieties present in neurodegenerative diseases such as stroke, hypovolemic shock, traumatic shock, reperfusion injury, multiple sclerosis, AIDS, associated dementia; neuron toxicity, Alzheimer's disease, head trauma, adult respiratory disease (ARDS), acute spinal cord injury, Huntington's disease, and Parkinson's Disease.

Signal transduction cascades operate, in part, through sequential phosphorylation events mediated by protein kinases. These covalent events are critical in transducing signals from the outside of the cell to the nucleus, where they bring about changes in gene expression. The inventors claim that activation (i.e., phosphorylation) of a specific protein kinase in any specific transduction pathway could be analyzed by hybridization of a cell extract to a peptoid microarray. The idea is that a chemically modified protein would evince a pattern of binding to the array distinct from that of the unmodified protein. The patterns of interest could be visualized by subsequent hybridization of the array with a labeled antibody (or an unlabeled antibody and a labeled secondary) that did not distinguish between the different forms of the protein kinase. This would remove the requirement for phospho-form-specific antibodies, which is a major technical hurdle currently in mapping signal transduction cascades. Note that this does not require the subsequent analysis of proteins or peptides bound to each feature by mass spectrometry or any other tool and does not require the identification in the mass spectrum of peaks corresponding to phosphorylated or otherwise modified peptides.

III. SCREENING ASSAYS

The present invention also contemplates the screening of cyclic peptoids for their ability to bind to various therapeutic targets and cause therapeutic effects. Various assays can be conducted, such as in vitro and in vivo binding and inhibition assays, as well as assays for particular therapeutic efficacy, e.g., anti-cancer activity.

The present invention provides methods of screening for agents that bind various therapeutic targets. In an embodiment, the present invention is directed to a method of:

(a) providing a candidate peptoid;

(b) contacting the peptoid with therapeutic target; and (c) determining the binding of the candidate peptoid with a therapeutic target, wherein binding to a binding target identifies the candidate as a putative modulator of the therapeutic target.

Measuring binding can be direct, by identifying a target-peptoid complex, by identifying a candidate peptoid that associates with, or by assessing the inhibition of binding of a labeled peptoid or other ligand to binding target.

It will, of course, be understood that all the screening methods of the present invention are useful in themselves notwithstanding the fact that effective candidates may not be found. The invention provides methods for screening for such candidates, not solely methods of finding them. It will also be appreciated that the present invention comprises high affinity ligands or binding moieties found or discovered using the assays or microassays described herein. These high affinity ligands, including the cyclic peptoid ligands, are useful as pharmaceuticals in their own right. The invention comprises a high affinity cyclic peptoid ligand identified by the process claimed herein for screening cyclic peptoid libraries. The high affinity cyclic peptoid ligand identified hereunder may be a vaccine or drug.

Various cells that express a binding target can be utilized for screening of candidate substances. A number of cells and cell lines are available for use in cell based assays. Cells include, but are not limited to human vascular endothelial cells (HUVECs) and various cancer cell lines, as well as primary cells from individuals. Depending on the assay, culture may be required. Labeled candidate peptoids may be contacted with the cell and binding assessed therein. Various readouts for binding of candidate substances to cells may be utilized, including ELISA, fluorescent microscopy and FACS.

The present invention particularly contemplates the use of various animal models. For example, various animal models of cancer may be used to determine if the candidate peptoids inhibit cancer cell growth, metastasis or recurrence, or affects its ability to evade the effects of other drugs. Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by oral, sublingual, intratracheal instillation, bronchial instillation, intradermal, subcutaneous, intramuscular, intraperitoneal or intravenous injection. The present invention also contemplates pharmaceutical compositions comprising high affinity ligands selected from cyclic peptoids identified through the screening methods claimed herein and a pharmaceutically acceptable excipient. These compositions may also be delivered through any of the means identified above for administering the test compounds to an animal.

A. Cell Based Screening Formats

Cell based screening assays can be used to identify target-specific ligands, such as cyclic peptoids. Cells having differential characteristics, such as the presence or absence of a cell surface receptor, but otherwise identical, are differentially labeled (e.g., two different colored quantum dots). The cells are then mixed in an approximately 1:1 ratio and then exposed to a library of molecules displayed on a substrate. After appropriate incubation and washing, the beads that bind only one color cell are picked. The beads are treated to remove the cells and other debris, and the bound molecule is identified by an appropriate analytical technique. This two-color assay demands extremely high specificity. If the bead-displayed molecule binds any other molecule on the cell surface other than the target, then both colored cells will be retained and the molecule will not be identified as a hit. See Udugamasooriya et al. (2008).

The assay can be modified to accommodate a variety of different formats. For example, a three cell types assay can be used to distinguish ligands that bind to highly related molecules. For example, where two receptors are almost identical, cells are provided that are null or have one or the other related receptor. Each cell type (null, receptor 1-containing and receptor 2-containing) is labeled with a different agent (e.g., colored quantum dot). The cells are mixed together in an approximately 1:1:1 ratio and exposed to a bead library. Beads that bind only one color cell are picked and the chemical that they display is characterized.

Examples of structures that can be differentiated include antibody or T-cell receptors of various immune cells, growth factor receptors, cell matrix proteins, lectins, carbohydrates, lipids, cell surface antigens from various pathogens. Additionally, the cells could differ not in the composition of the cell surface molecules, but in their arrangement. For example on one cell type, two given cell surface molecules might associate with one another and provide a unique binding site for a ligand that might be absent from a different cell type where these receptors do not associate. Labeling can utilize calorimetric, fluorometric, bioluminescent or chemiluminescent labels.

The assay can also be modified to identify ligands that bind to cells present in only one of two or more distinct cell populations. For example, all CD4+ T cells from a healthy individual or group of individuals could be labeled with one colored dye and the CD4+ T cells from an individual or group of individuals with an autoimmune disease could be labeled with a different colored dye. The two populations of T cells could then be mixed with the bead library and beads retaining only cells from the autoimmune patients could be selected. These T cells would be candidates for the autoimmune T cells that display the T cell Receptor (TCR) that binds the autoantigen and contributes to disease, since these cells should only be abundant in the autoimmune samples and not in cells obtained from healthy individuals.

In another application, the two or more cell populations could differ solely in the presence or absence of a genetic mutation that might result in a change in the composition and/or organization of molecules on the cell surface.

IV. KITS

Any of the compositions described herein may be comprised in a kit. In a non-limiting example, cyclic peptoids, cyclic peptoid arrays and related support(s), buffers, linkers, and reagents are provided in a kit. The kit may further comprise reagents for processing a sample and/or sample components. The kit may also comprise reagents that may be used to label various components of an array or sample, with for example, radio isotopes or fluorophors.

Kits for implementing methods of the invention described herein are specifically contemplated. In some embodiments, there are kits for synthesis, processing, and detection of cyclic peptoid arrays.

Regents for the detection of sample component binding can comprise one or more of the following: array substrate; cyclic peptoids; and/or detection reagents.

The components of the kits may be packaged either in aqueous media or in lyophilized form. The container means of the kits will generally include at least one vial, test tube, plate, flask, bottle, array substrate, syringe or other container means, into which a component may be placed, and preferably, suitably attached. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing binding elements or reagents for synthesizing such, and any other reagent containers in close confinement for commercial sale. Such containers may include injection or blow molded plastic containers into which the desired vials are retained.

When components of the kit are provided in one and/or more liquid solutions, the liquid solution is typically an aqueous solution that is sterile and proteinase free. In some cases proteinaceous compositions may be lyophilized to prevent degradation and/or the kit or components thereof may be stored at a low temperature (i.e., less than about 4° C.). When reagents and/or components are provided as a dry powder and/or tablets, the powder can be reconstituted by the addition of a suitable solvent. It is envisioned that the solvent may also be provided in another container means.

V. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Materials and Equipments.

All commercial reagents were used as obtained without further purification. O-tert-Butyl-2-amino ethanol was purchased from CSPS Pharmaceuticals. Methylamine was used as 2 M solution in THF. Polystyrene AM RAM macrobead (500-560 μm; 0.52 mmol/g) and Rink Amide AM LL (100-200 mesh, 0.35 mmol/g) resins were obtained from Rapp Polymere and Novabiochem, respectively. NMR spectra were recorded on a Varian 300 MHz spectrometer. Preparative HPLC was performed on a Waters binary HPLC system with a C18 reverse-phase column with the gradient elution of water/acetonitrile with 0.1% TFA. MS and tandem MS (MALDI-TOF) were performed on a Voyager-DE PRO biospectrometry workstation and 4700 Proteomics Analyzer (Applied Biosystems) with α-cyano-4-hydroxycinnamic acid as a matrix, respectively. The synthesis of peptides was performed in a New Brunswick Scientific Innova 4000 incubator shaker. The synthesis of peptoids under microwave conditions was performed in a 1000 W Whirlpool microwave oven (model MT1130SG) with 10% power. Standard glass peptide synthesis vessels (Chemglass) were used for the synthesis in the incubator shaker and in the microwave oven. Microarrays were prepared on maleimide-functionalized glass slides by using SpotArray 72 Microarray Printing System (PerkinElmer). Hybridized microarrays were scanned with a GenePix 4000B scanner.

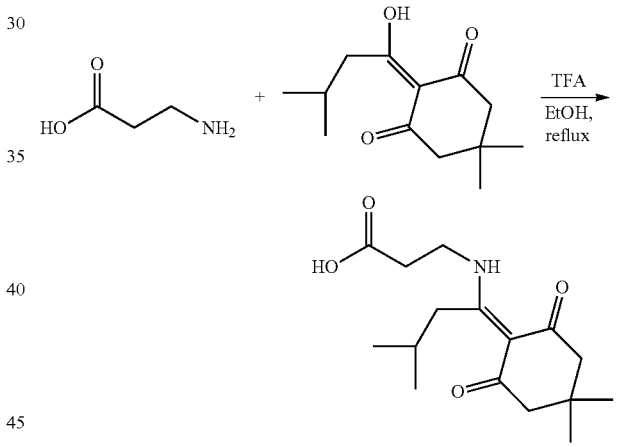

Synthesis of ivDde-β-Ala-OH.

To a stirred suspension of H-β-Ala-OH (1.02 g, 11.4 mmol) and ivDde-OH (5 ml, 22.9 mmol) in EtOH was added TFA (88 μL, 1 mmol) at room temperature.[1] The mixture was then refluxed for 24 hours. After the solvent was evaporated in vacuo, a crude product was purified by column chromatography with $CH_3OH/CH_2Cl_2$ (0.1% TFA) gradient to afford ivDde-β-Ala-OH (3.3 g, 97.6%). $^1$H NMR (CDCl$_3$) δ 1.02 (m, 12H), 1.90-2.03 (m, 1H), 2.39 (s, 4H), 2.75 (t, J=6.0 Hz, 2H), 3.06 (br d, J=6.0 Hz, 2H), 3.78 (q, J=6.0 Hz, 2H); $^{13}$C NMR (CDCl$_3$) δ 22.8, 28.4, 29.4, 30.2, 34.1, 37.4, 39.6, 52.9, 107.4, 173.0, 177.2; MS (MALDI): m/z: calcd for $C_{16}H_{26}NO_4$ 296.2; found 296.5 [M+H]$^+$.

Cyclization Reactions of Peptoids on Bead.

Preliminary cyclization reactions of peptoids on bead were tested under various conditions. The typical procedure with PyBOP which gave the best results is as follows. The cyclization yields also depended on the length of the peptoid with high yields requiring at least six monomeric units. Fmoc-Cys (Trt)-OH and Fmoc-Glu(O-2-PhiPr)—OH were coupled to the Rink Amide AM resin sequentially by using Fmoc chemistry. The synthesis of peptoids was performed by employing a microwave-assisted submonomer protocol.[2] 2-PhiPr group was deprotected with 1% TFA and 2% triisopropylsilane in DCM for 2*30 min. After the resins were thoroughly washed with 5% DIPEA in DCM and DCM, cyclization was carried out under the conditions of PyBOP (3 eq.), HOBt (3 eq.) and DIPEA (10 eq.) in DMF for 2*10 h. Cyclic peptides were confirmed by MALDI-MS and HPLC after cleavage from beads.

General Procedure for the Construction of Encoded Cyclic Peptoid Libraries.

Polystyrene AM RAM macrobeads in DMF were allowed to swell at room temperature for 1 h. After DMF was drained, the beads were incubated with 20% piperidine for 30 min. The beads were thoroughly washed with DMF (8×3 mL) and then treated with Fmoc-β-Ala-OH (5 eq.) by using HBTU (5 eq.), HOBt (5 eq.) and DIPEA (10 eq.) in DMF for 2 h. After The beads were thoroughly washed with DMF (8×3 mL) and incubated with 20% piperidine for 30 min, they were thoroughly washed with DMF (8×3 mL) and then treated with ivDde-β-Ala-OH (0.6 eq.) and Fmoc-Cys(Trt)-OH (4 eq.) by using HBTU (4.6 eq.) and NMM (10 eq.) in DMF. After 2 h, the beads were thoroughly washed with DMF (8×3 mL) and then treated with $Ac_2O$ (10 eq.) and DIPEA (10 eq.) in DMF for 1 h to block possible unreacted amines. After the beads were thoroughly washed with DMF (8×3 mL) and Fmoc group was selectively removed with the treatment of 20% piperidine for 30 min, they were again coupled with Fmoc-β-Ala-OH (5 eq.) by using HBTU (5 eq.), HOBt (5 eq.) and DIPEA (10 eq.) in DMF for 2 h. After the beads were thoroughly washed with DMF (8×3 mL) and incubated with 20% piperidine for 30 min, they were treated with Fmoc-Glu(O-2-PhiPr)—OH (3 eq.) by using HATU (3 eq.), HOBt (3 eq.) and DIPEA (10 eq.) in DMF. After 2 h, the beads were thoroughly washed with DMF (8×3 mL) and then treated with $Ac_2O$ (10 eq.) and DIPEA (10 eq.) in DMF for 1 h to block possible unreacted amines. ivDde and Fmoc groups were removed with the successive treatments of 2.5% hydrazine for 2*10 min and 20% piperidine for 30 min. After the beads were thoroughly washed with DMF (8×3 mL), split-and-mix linear peptoid libraries consisting of 7-mer peptoids were prepared by using bromoacetic acid and primary amines such as methylamine, allylamine, 2-methoxyethylamine, O-tert-butyl-2-amino ethanol, piperonylamine, fufurylamine, benzylamine, 1-N-tert-butyloxycarbonyl-1,4-diaminobutane based on a microwave-assisted submonomer protocol.[2] 2-PhiPr group was selectively deprotected with 1% TFA and 2% triisopropylsilane (TIS) in DCM for 2*30 min. After the resins were thoroughly washed with 5% DIPEA in DCM and DCM, cyclization was carried out under the conditions of PyBOP (3 eq., ~30 mM), HOBt (3 eq. ~30 mM) and DIPEA (10 eq.) in DMF for 2*10 h. Cyclization yields depended on the residues at N-terminal. Cyclic peptoid libraries consisting of Nmea at the N-terminal afforded much better results with almost complete cyclization. Cyclic peptoids were confirmed by MS, tandem MS (MALDI) or HPLC after cleavage from the resin under the conditions of 95% TFA and 5% TIS for 1.5 h.

Hybridization of Biotin-Labeled Cyclic Peptoids Microarray and Streptavidin-Cy3.

Microarrays consisting of biotin-labeled cyclic peptoids with Nmea at the N-terminal were prepared. Biotin-labeled cyclic peptoids were spotted onto maleimide-functionalized glass slides with 3-fold serial dilution of about 2 mM solution. Microarrays were equilibrated with 1×TBST (50 mM Tris/150 mM NaCl/0.1% Tween 20, pH 8.0) for 30 mM at 4° C. Microarray slides were incubated with Streptavidin-Cy3 (10 μL, Sigma) and BSA (50 μL of 2 mg/mL) in 1×TBST (total 1 mL solution) with gentle shaking for 45 min at 4° C. The slides were washed with 1×TBST (3×5 min) at 4° C., and then dried by centrifugation. Hybridized microarrays were scanned with a GenePix 4000B scanner.

Figure 2:
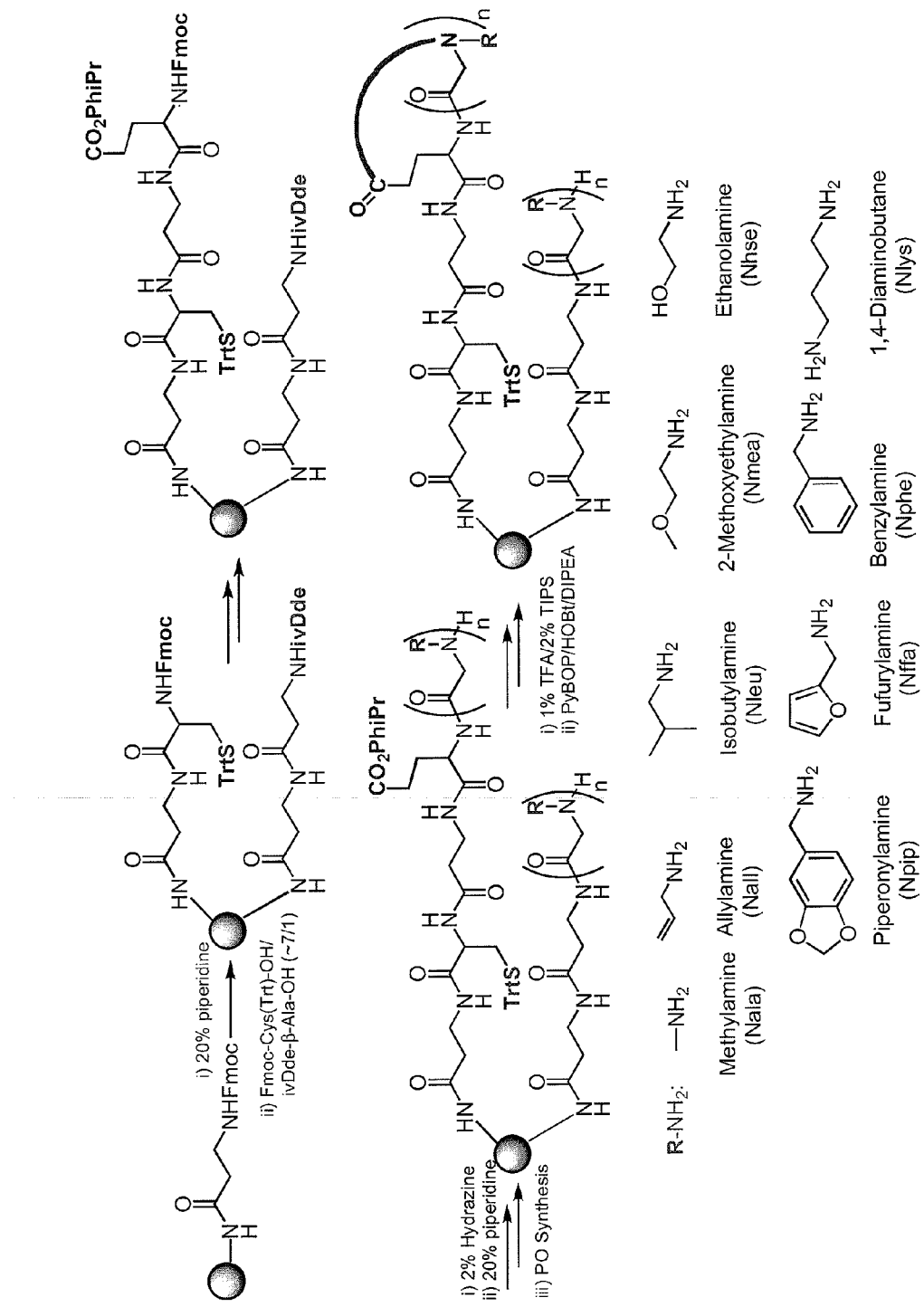
FIG. 2—Synthesis of the encoded cyclic peptoid library via the one bead two compound strategy. The amines employed in the sub-monomer peptoid synthesis are shown at the bottom of the figure (one of the amines in 1,4-diaminobutane and a hydroxyl group in ethanolamine were protected).

The inventor prepared ten peptoids of the form: β-Ala-Cys-Glu(Biotin)-cyclo(Glu-X-X-X-X-X-X-Nmea) (see FIGS. 3A-C), where biotin-Glu bears a side chain-conjugated biotin and X was derived from one of the amines shown in FIG. 2. The molecules were cleaved from the resin and analyzed by HPLC and tandem MS. In each case, the inventors were able to easily sequence the linear species by tandem mass spectrometry. Moreover, all of the detectable Cys-containing molecules were in the cyclic form.

Figure 3A:
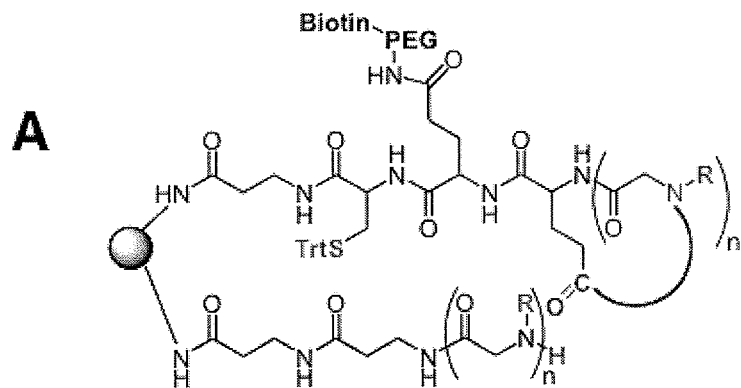
FIGS. 3A-3C—Attachment of Cys-containing cyclic peptoid to a maleimide-activated glass slide.
Figure 3B:
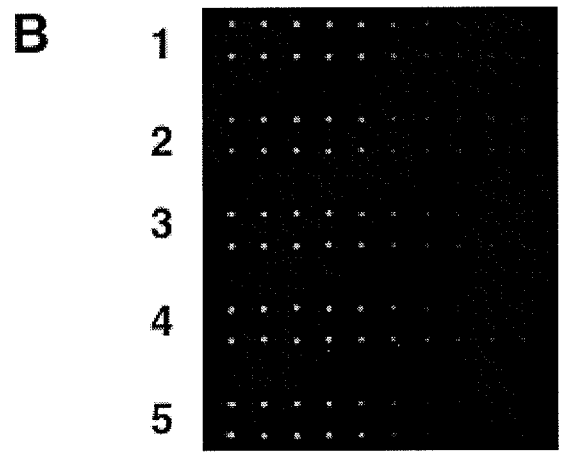
Figure 3C:
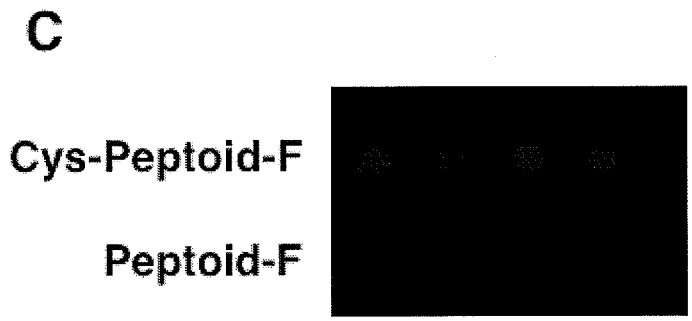
Figure 4:
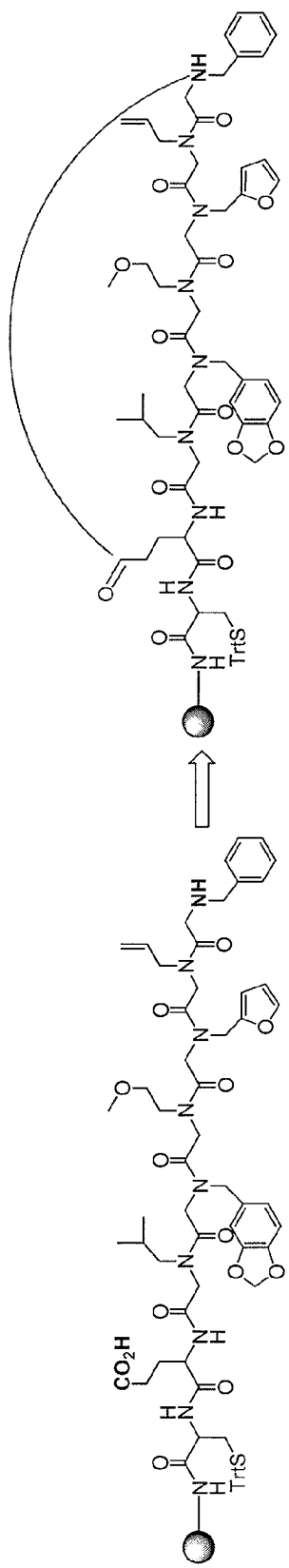
FIG. 4—Cyclization reaction of model peptoid on bead.
Figure 5:
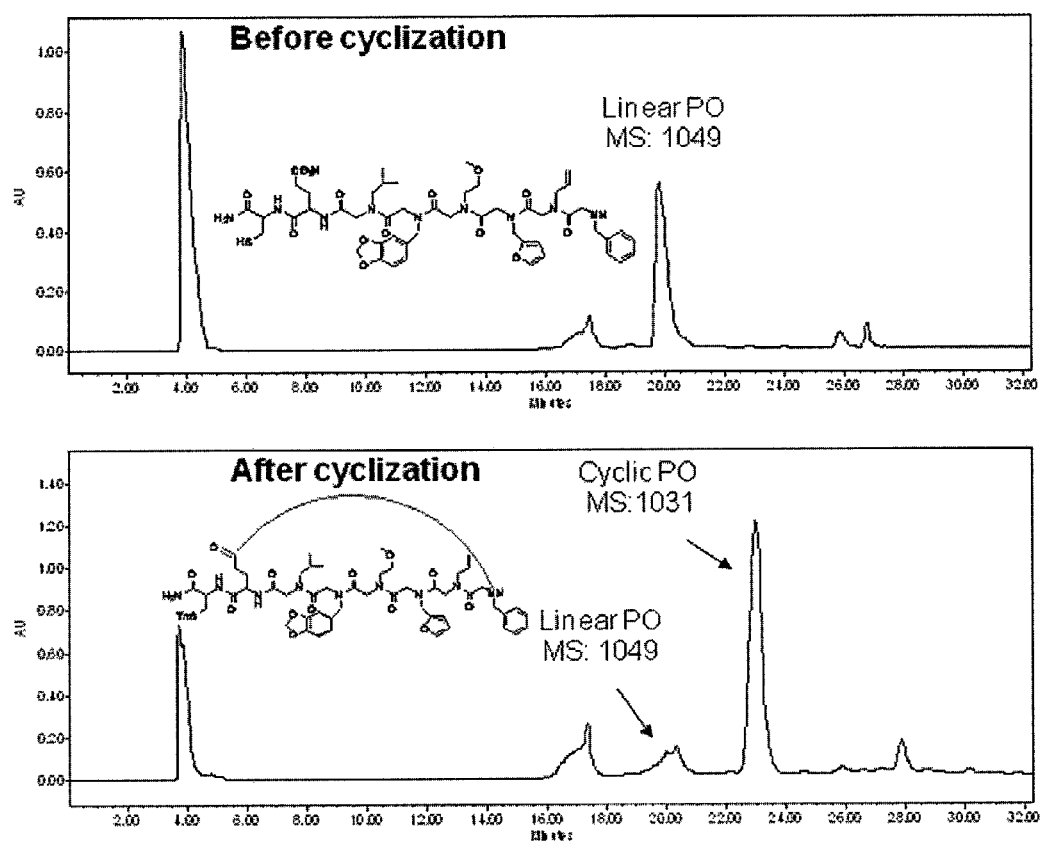
FIG. 5—RP-HPLC traces of peptoids before cyclization and after cyclization by using PyBOP.
Figure 6:
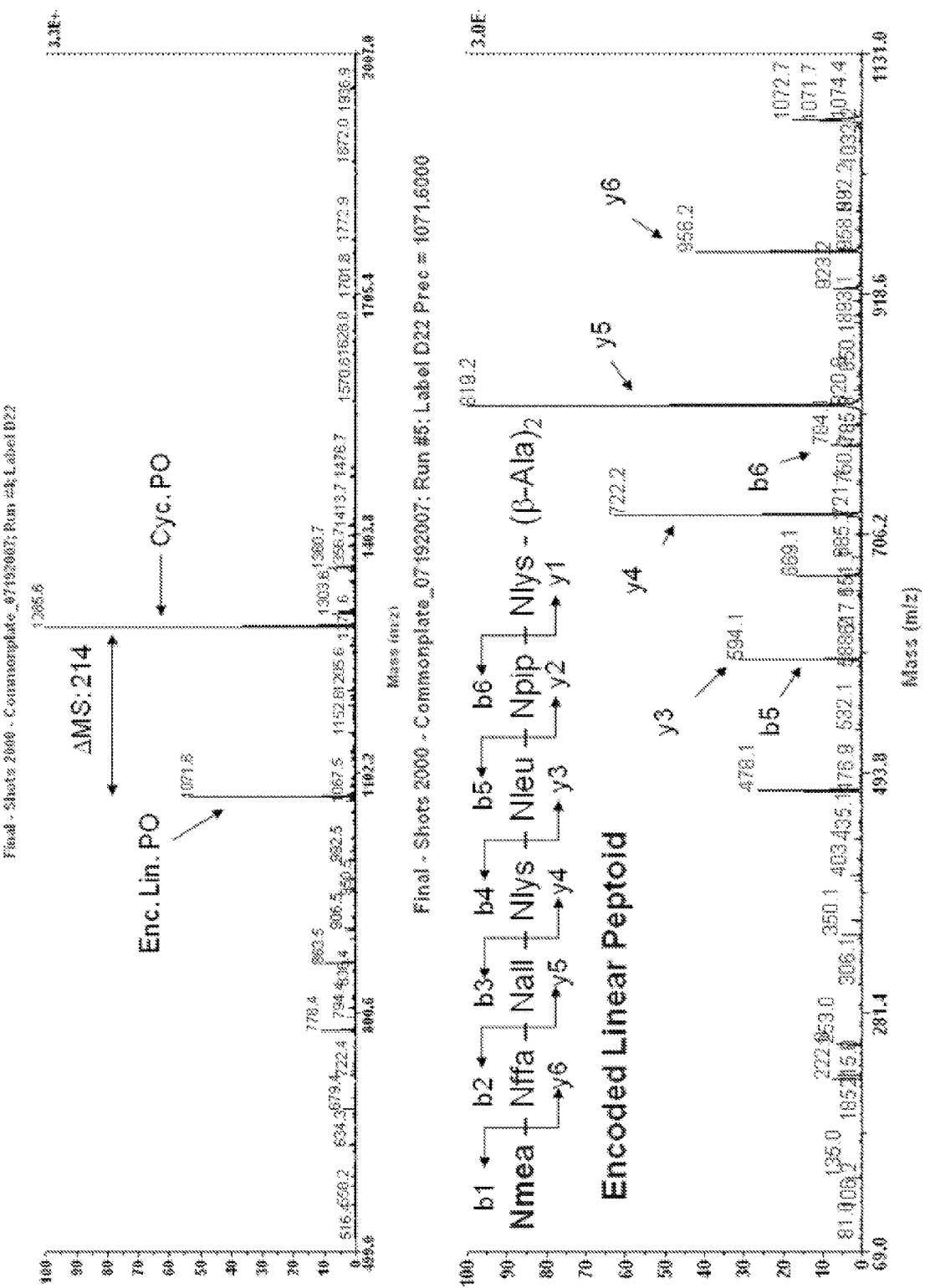
FIG. 6—Sequence analysis for random members from cyclic peptoids library with Nmea at N-terminal: (a) Nmea-Nffa-Nall-Nlys-Nleu-Npip-Nlys.
Figure 7:
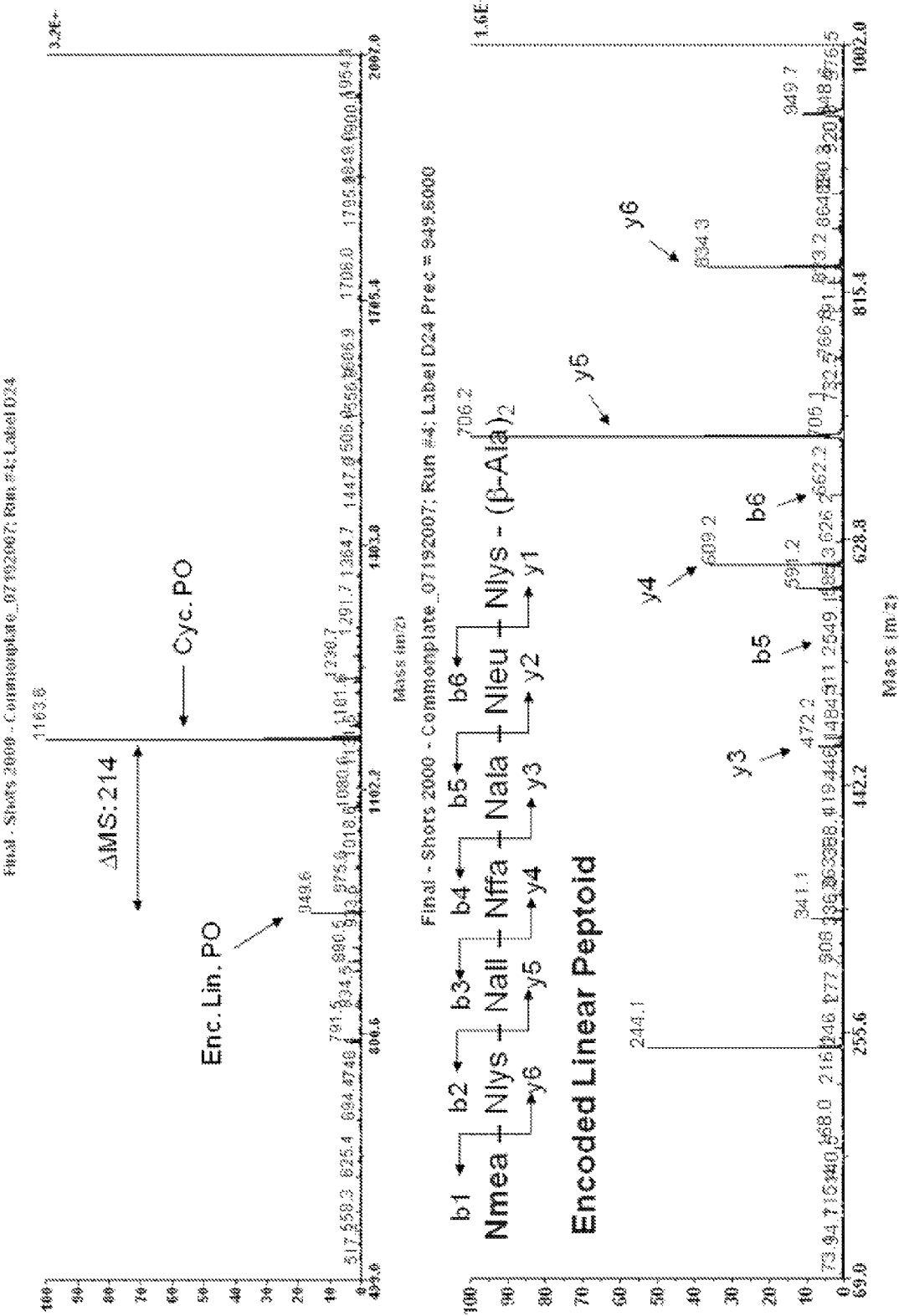
FIG. 7—Sequence analysis for random members from cyclic peptoids library with Nmea at N-terminal: (b) Nmea-Nlys-Nall-Nffa-Nala-Nleu-Nlys.
Figure 8:
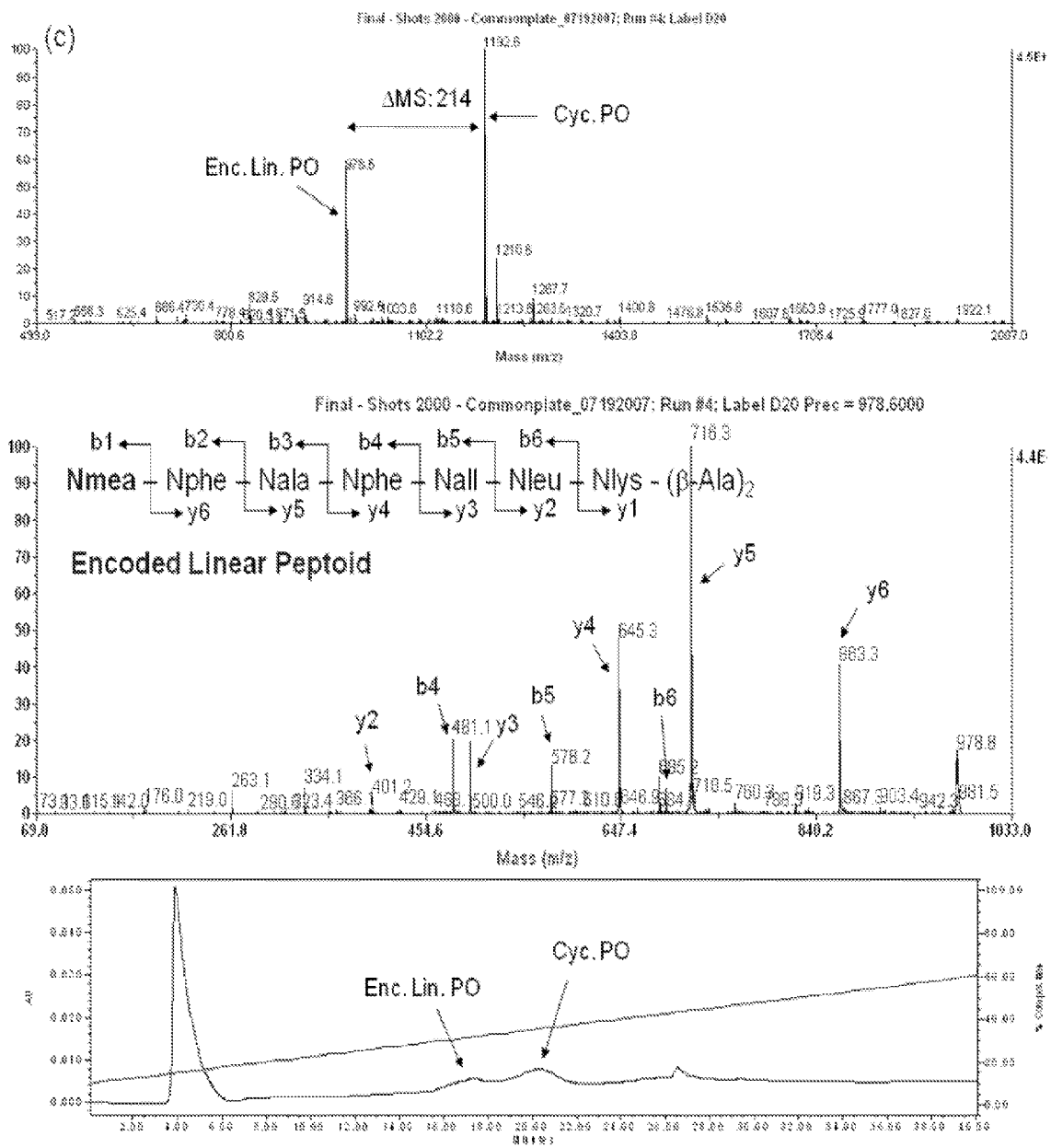
FIG. 8—Sequence analysis for random members from cyclic peptoids library with Nmea at N-terminal: (c) Nmea-Nlphe-Nala-Nphe-Nall-Nleu-Nlys. RP-HPLC trace of cyclic peptoid and encoded linear peptoid are also shown.
Figure 9:
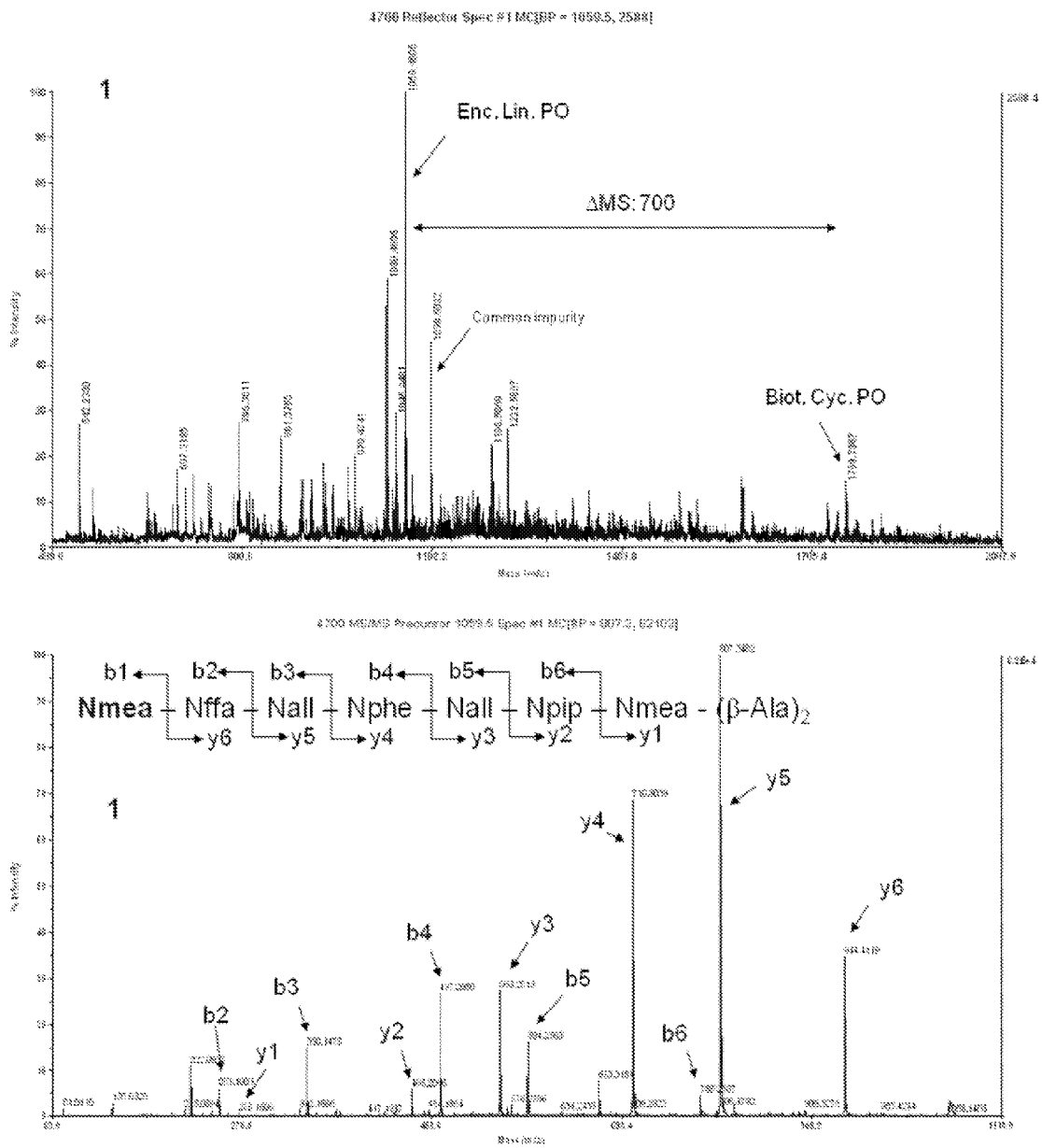
FIG. 9—MS, MS/MS data for biotin-labeled cyclic peptoid (1) with Nmea at N-terminal.
Figure 10:
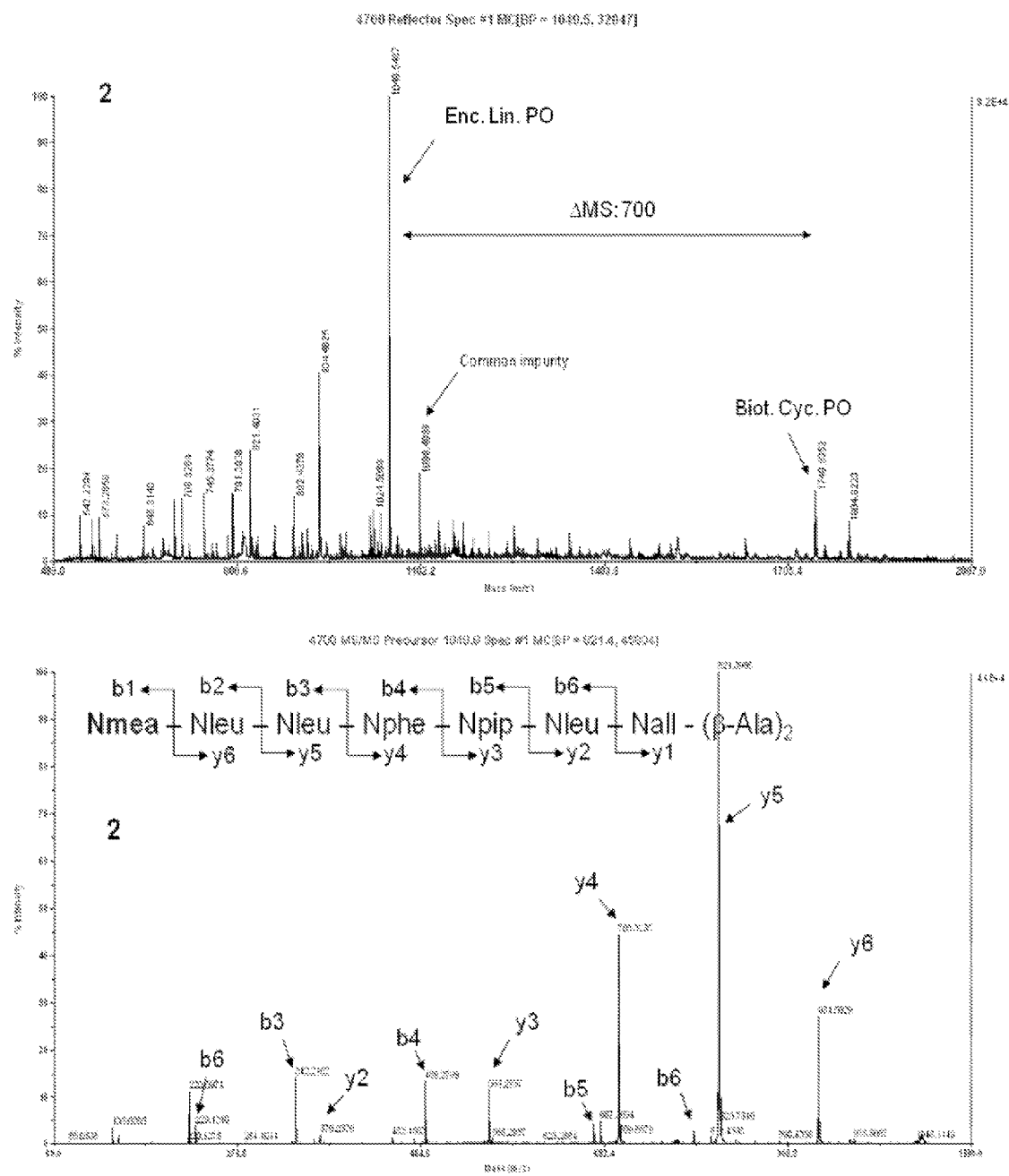
FIG. 10—MS, MS/MS data for biotin-labeled cyclic peptoid (2) with Nmea at N-terminal.
Figure 11:
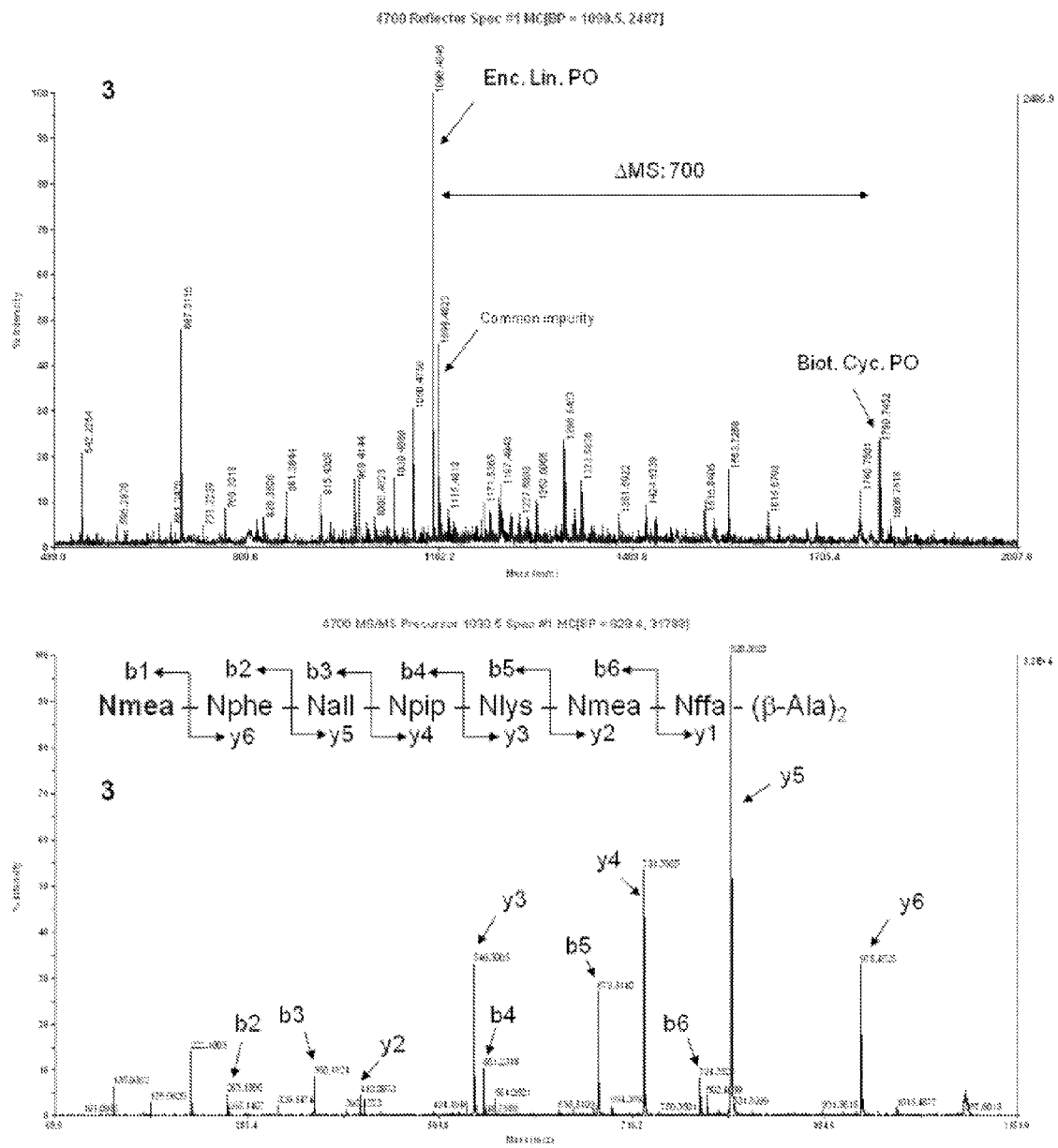
FIG. 11—MS, MS/MS data for biotin-labeled cyclic peptoid (3) with Nmea at N-terminal.
Figure 12:
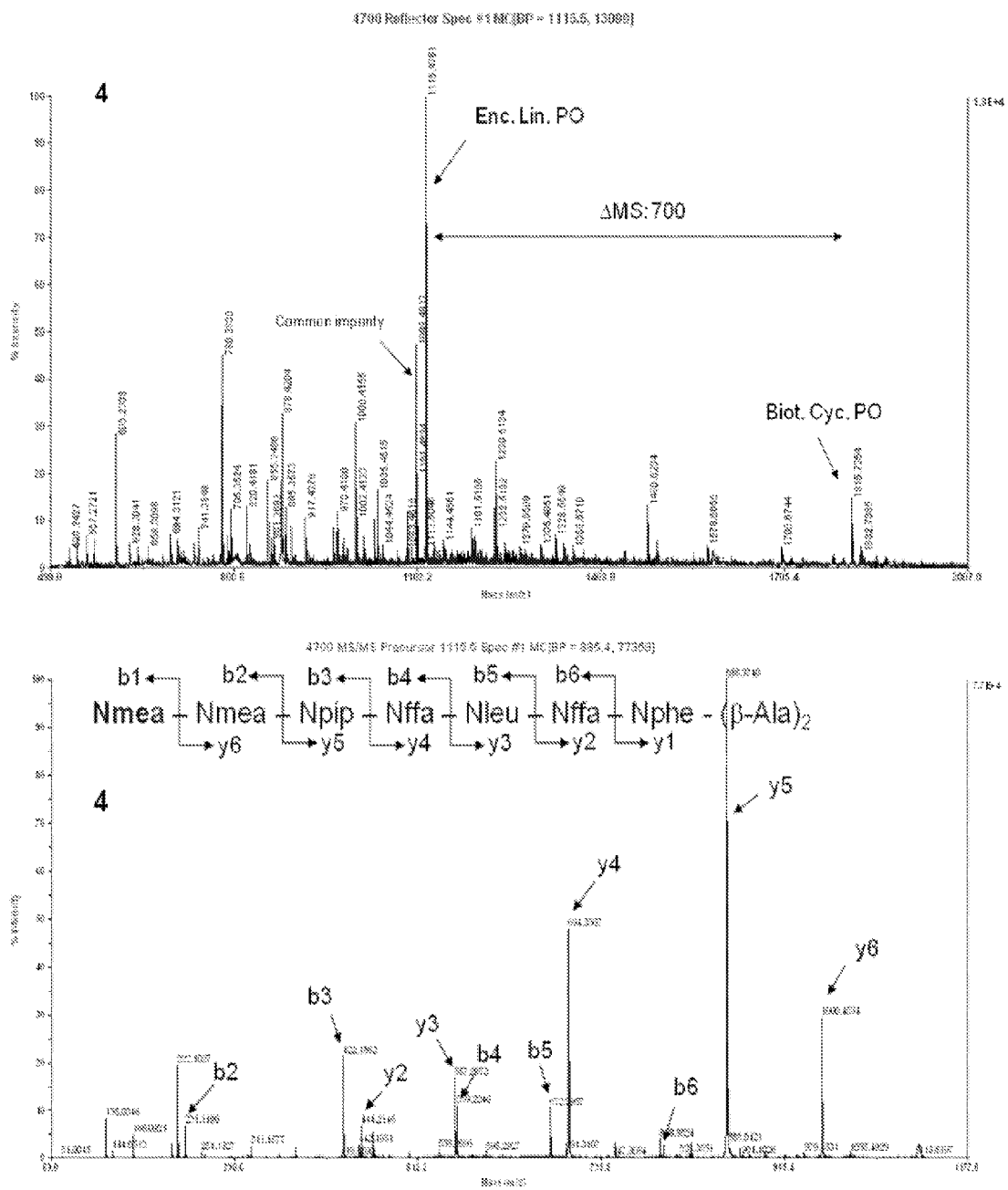
FIG. 12—MS, MS/MS data for biotin-labeled cyclic peptoid (4) with Nmea at N-terminal.
Figure 13:
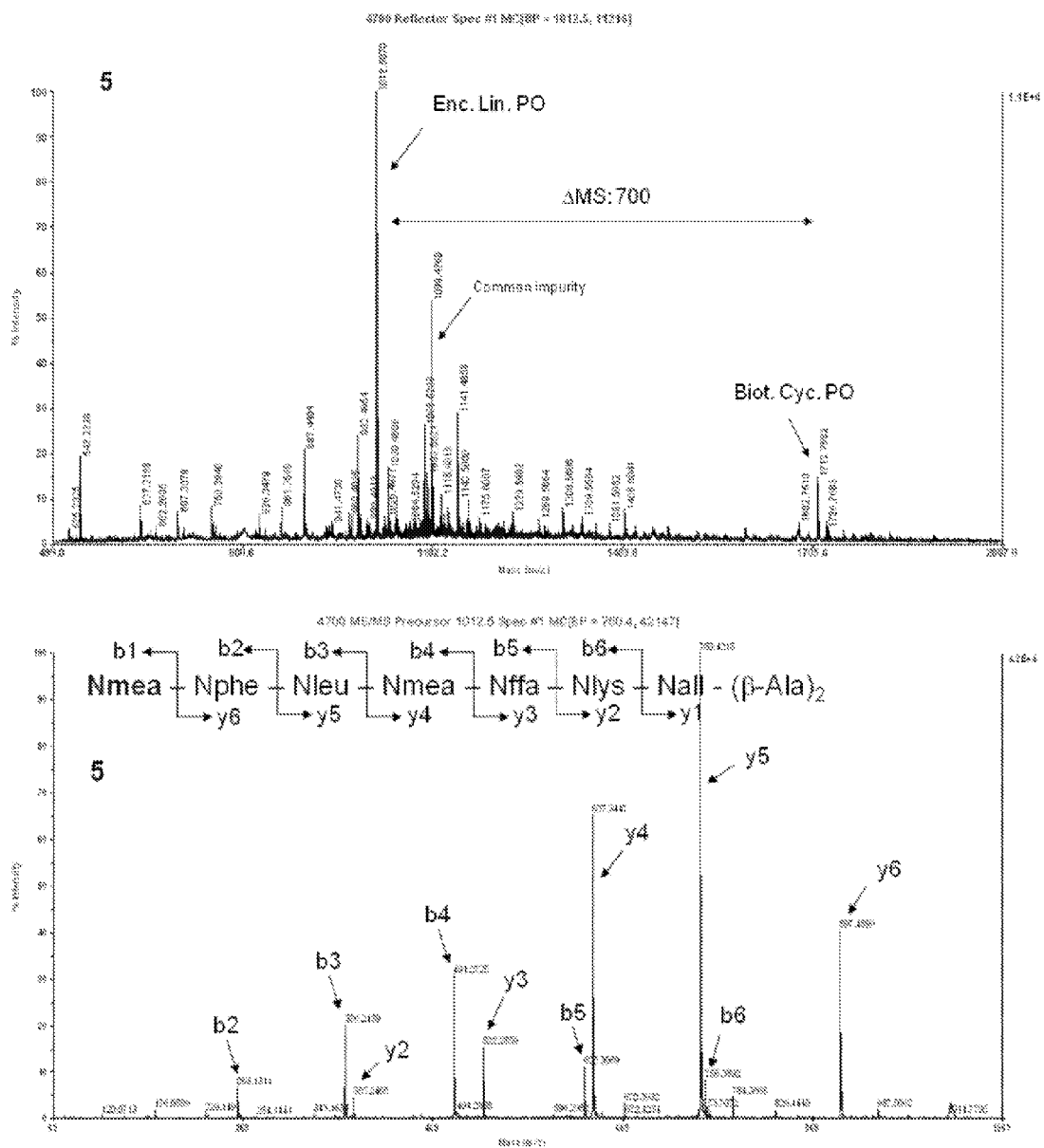
FIG. 13—MS, MS/MS data for biotin-labeled cyclic peptoid (5) with Nmea at N-terminal.
Figure 14:
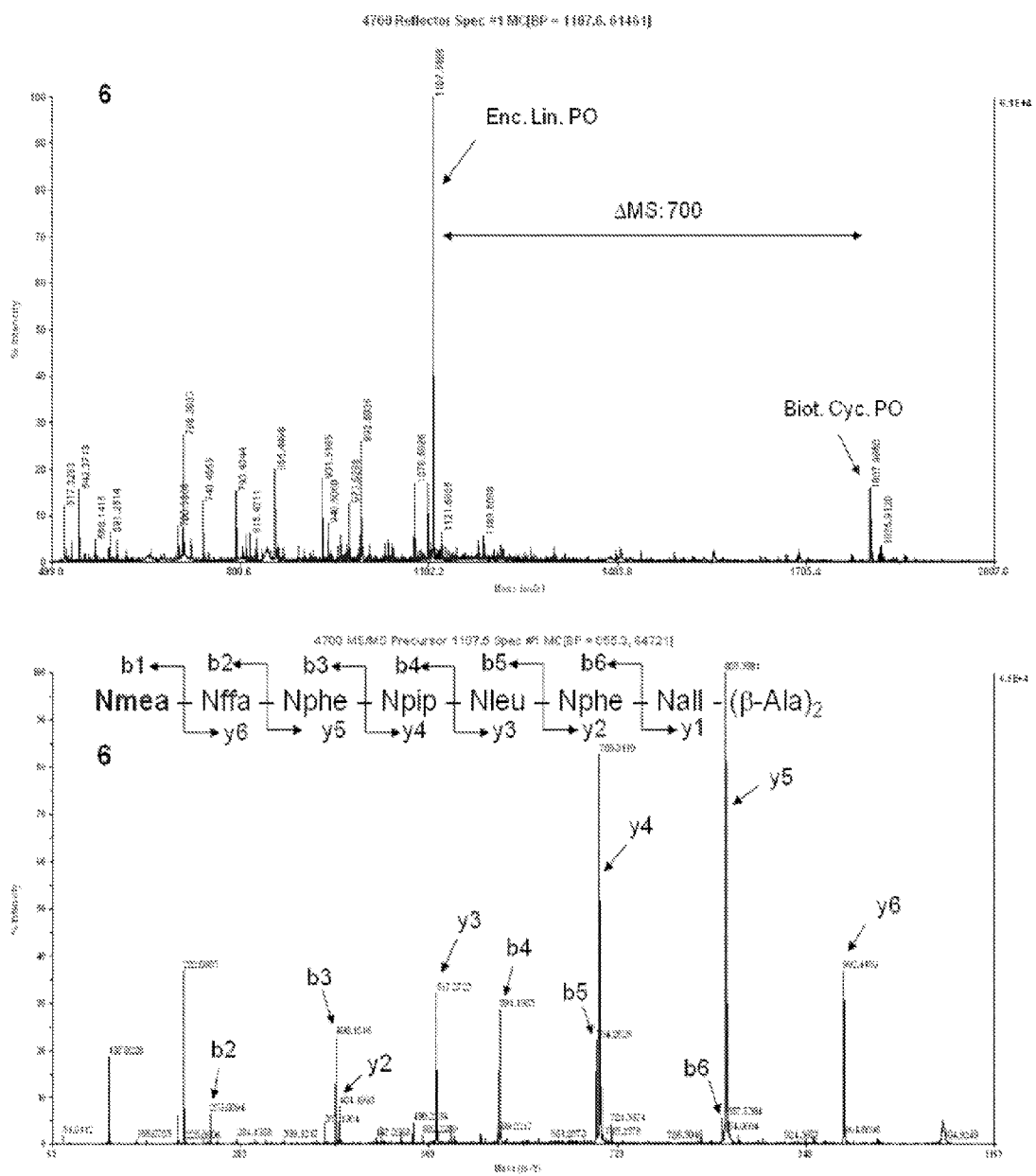
FIG. 14—MS, MS/MS data for biotin-labeled cyclic peptoid (6) with Nmea at N-terminal.
Figure 15:
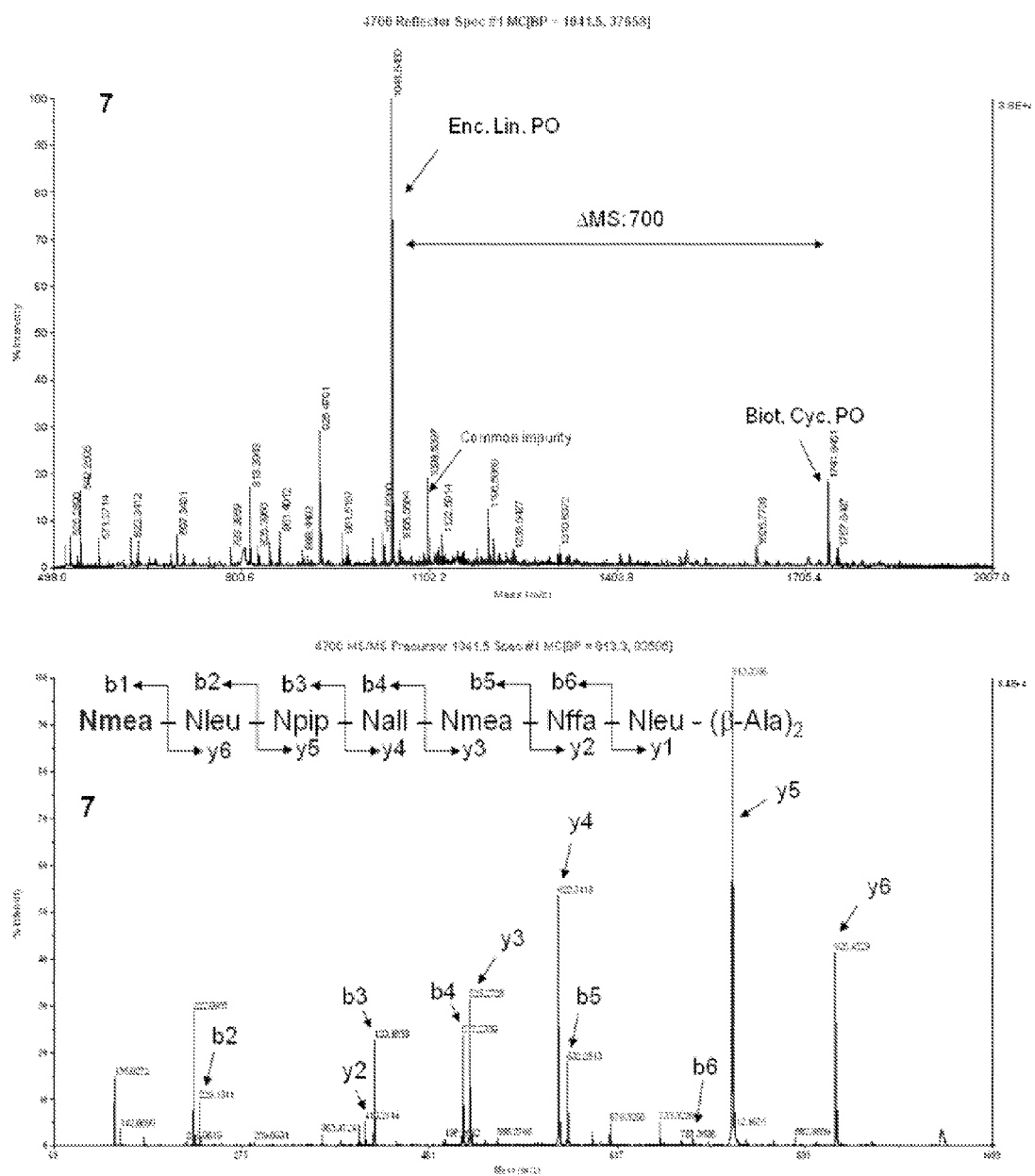
FIG. 15—MS, MS/MS data for biotin-labeled cyclic peptoid (7) with Nmea at N-terminal.
Figure 16:
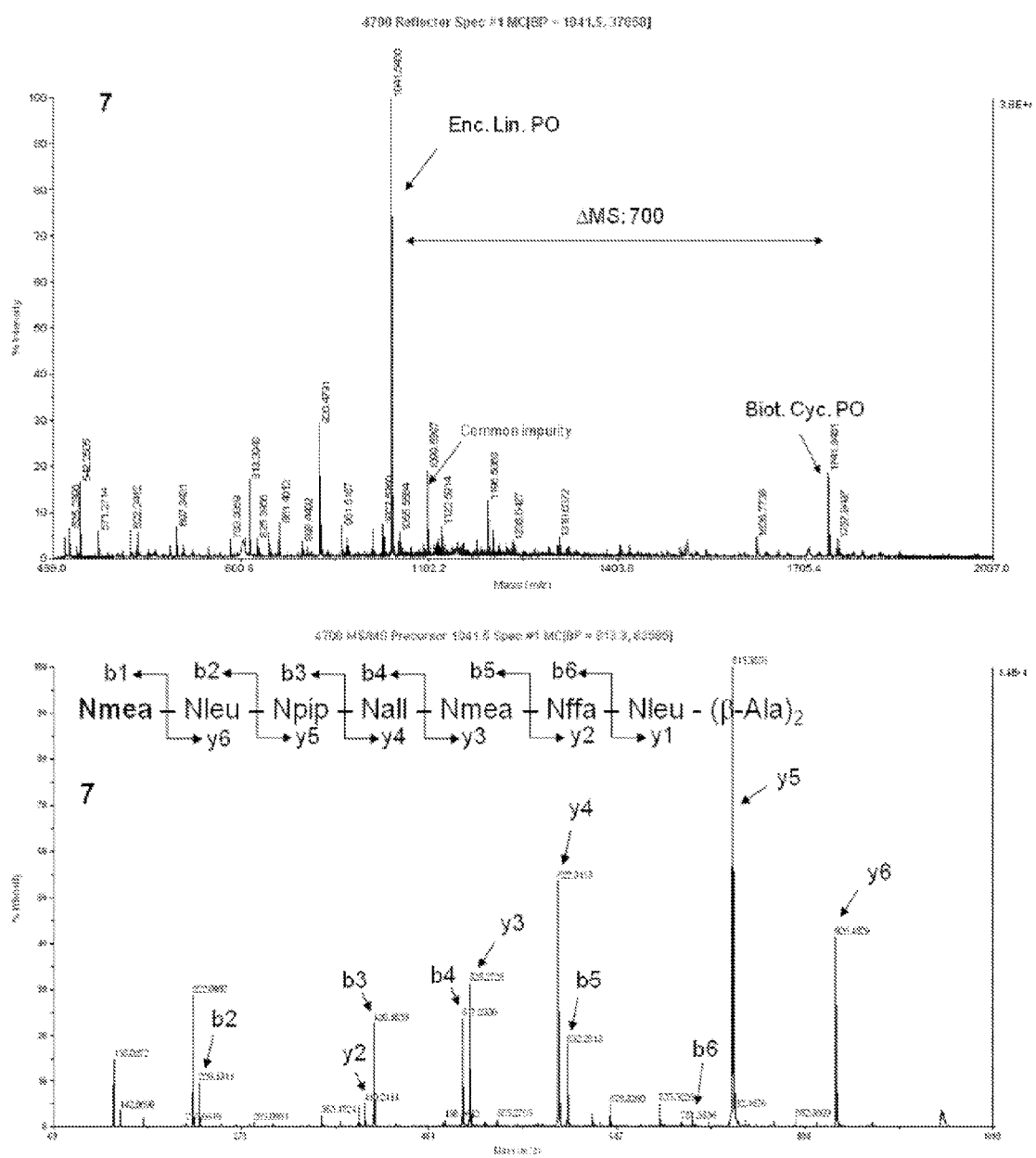
FIG. 16—MS, MS/MS data for biotin-labeled cyclic peptoid (8) with Nmea at N-terminal.
Figure 17:
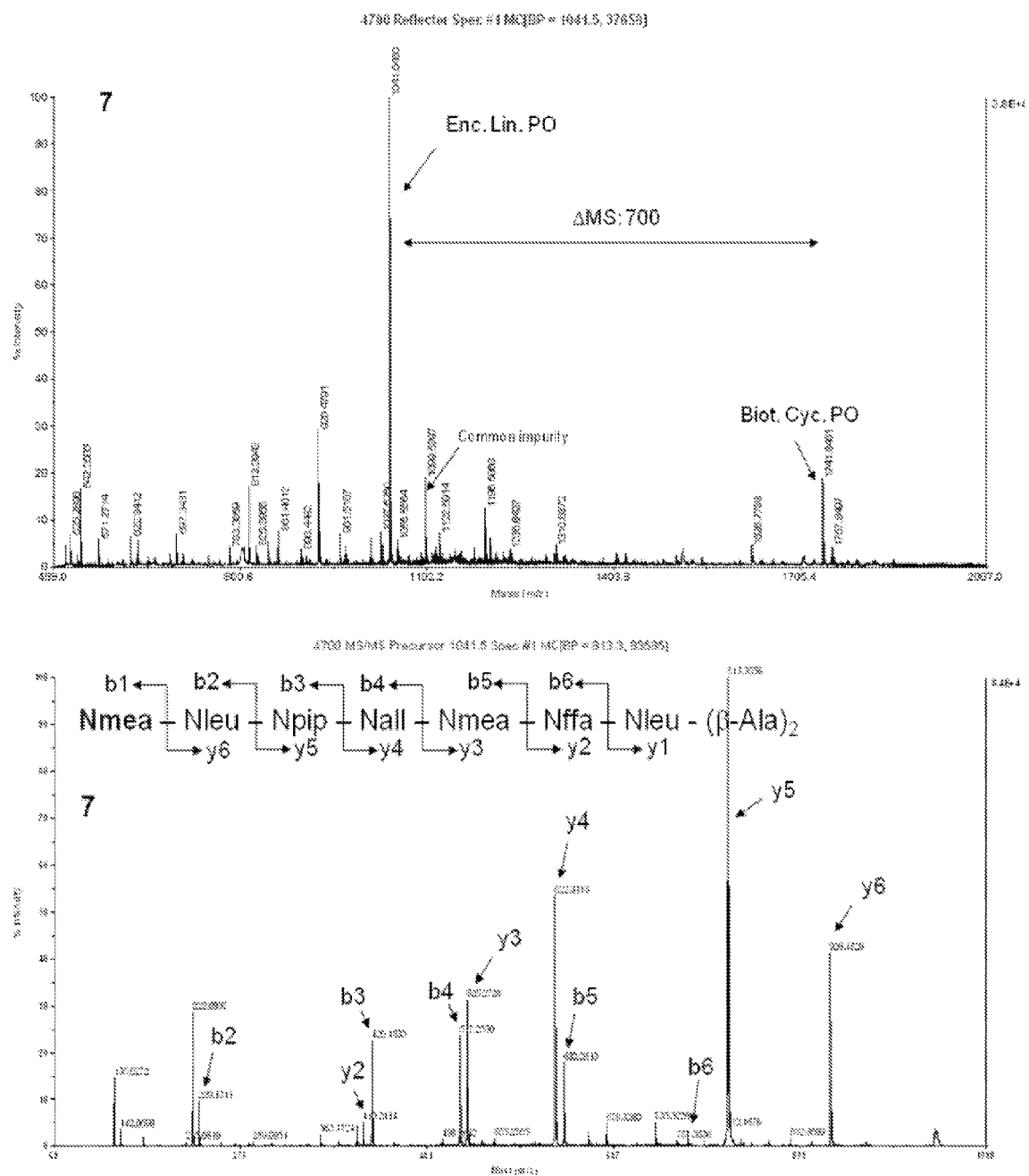
FIG. 17—MS, MS/MS data for biotin-labeled cyclic peptoid (9) with Nmea at N-terminal.
Figure 18:
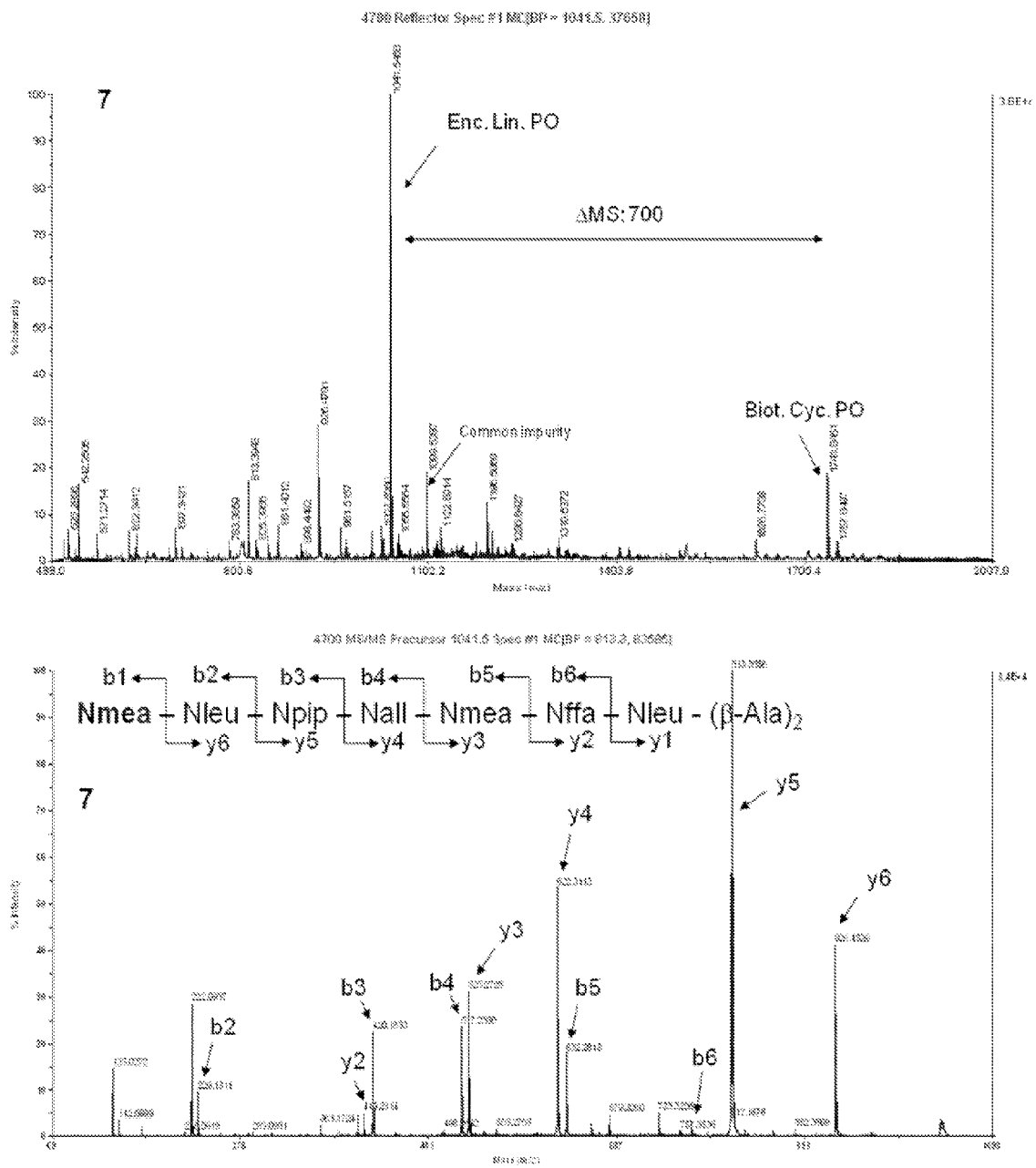
FIG. 18—MS, MS/MS data for biotin-labeled cyclic peptoid (10) with Nmea at N-terminal.

Serial dilutions of the five peptoids shown in FIGS. 3A-C were spotted robotically onto PEGylated, maleimide-activated glass microscope slides (Li et al., 2005) and the slides were then washed rigorously. In order to demonstrate the immobilization of the cyclic peptoids, the slides were incubated with Cy3-labeled Streptavidin and scanned. As expected, the amount of protein captured decreased as the amount of peptoid spotted decreased, confirming that the fluorescence is indeed due to specific capture of the protein by the peptoid (FIG. 3B). To demonstrate that the Cys residue retains the cyclic peptoid to the maleimide-derivatized slide, the inventors synthesized two fluorescein-conjugated linear peptoids that were identical except for the presence and absence of Cys. These were spotted onto a slide, which was then scanned after washing. As shown in FIG. 3C, detectable fluorescence was seen only where the Cys-containing peptoid was spotted. This study confirms that the linear encoding molecule (see FIG. 1) will not be retained on the slide when the mixture of it and the Cys-containing cyclic molecule are spotted onto the slide and thus will not interfere with screening experiments.

REFERENCES

The following references, to the extent that they provide exemplary procedural or other details supplementary to those set forth herein, are specifically incorporated herein by reference.

U.S. Pat. No. 4,680,338
U.S. Pat. No. 5,141,648
U.S. Pat. No. 5,563,250
U.S. Pat. No. 5,617,060
U.S. Publn. 2002/0137106
Alluri et al., *J. Amer. Chem. Soc.*, 125:13995-14004, 2003.
Alluri et al., *Mol. BioSystems*, 2:568-579, 2006.
Banerjee et al., *J Natural Prod.*, 71:492-496, 2008.
Figliozzi et al., *Methods Enzymol.*, 267:437-447, 1996.
Fouladi, *Cancer Invest.*, 24:521-527, 2006.
Hamada and Shioiri, *Chem. Rev.*, 105:4441-4482, 2005.
Ho et al., *Cin. Immunol. Immunopathol.*, 80:S40-S45, 1996.
Horn et al., *Bioconj. Chem.*, 15:428-435, 2004.
Johnson et al., In: *Biotechnology And Pharmacy*, Pezzuto et al. (Eds.), Chapman and Hall, NY, 1993.
Joo et al., *J. Amer. Chem. Soc.*, 128:13000-13009, 2006.
Lech-Maranda et al., *Mini Rev. Med. Chem.*, 7:1062-1069, 2007.
Li et al., *Chem. Comm.*, 581-583, 2005.
Lim et al., *J. Amer. Chem. Soc.*, 129:7750-7751, 2007.
Liu et al., *J. Amer. Chem. Soc.*, 124:7678-7680, 2002.
MacBeath et al., *J. Amer. Chem. Soc.*, 121:7967-7968, 1999.
Martin, *Pure Appl. Chem.*, 79:193-200, 2007.
Paulick et al., *J. Comb. Chem.*, 8:417-426, 2006.

PCT Pubin. WO 98/59360
Reddy and Kodadek, *Proc. Natl. Acad. Sci. USA*, 102:12672-12677, 2005.
Reddy et al., *Chem. & Biol.*, 11:1127-1137, 2004.
Rezai et al., *J. Amer. Chem. Soc.*, 128:14073-14080, 2006a.
Rezai et al., *J. Amer. Chem. Soc.*, 128:2510-2511, 2006b.
Satoh et al., *Biochem. Biophys. Res. Commun.*, 224, 438-443, 1996.
Schena et al, *Science*, 270:467-470, 1995.
Scott et al., *Proc. Natl. Acad. Sci. USA*, 96:13638-13643, 1999.
Shalon et al., *Genome Res.*, 6:639-645, 1996.
Shin et al., *J. Am. Chem. Soc.*, 129:3218-3225, 2007.
Simon et al., *Proc. Natl. Acad. Sci. USA*, 89:9367-9371, 1992.
Udugamasooriya and Spaller, *Biopolymers*, 89:653-667, 2008.
Udugamasooriya et al., *J. Amer. Chem. Soc.*, 130:5744-5752, 2008.
Uttamchandani et al., *Curr. Op. Chem. Biol.*, 9:4-13, 2005.
Venkatesh et al., *Proc. Natl. Acad. Sci. USA*, 97:761-766, 2000.
Wawrzynczak & Thorpe, *Cancer Treat Res.*, 37:239-51, 1988.
Xiao et al., *J. Comb. Chem.*, 9:592-600, 2007.
Zuckermann et al., *J. Med. Chem.*, 37:2678-2685, 1994.

What is claimed is:

1. A method of producing a cyclic peptoid/linear peptoid pair comprising:
    (a) independently coupling an array attachment group and a first peptoid initiator residue to a surface of a support;
    (b) coupling a cyclizing residue to the array attachment group;
    (c) coupling a second peptoid initiator residue to the cyclizing residue;
    (d) synthesizing concurrently a first peptoid coupled to the first initiator residue and a second peptoid coupled to the second initiator residue, wherein the first and second peptoid comprise identical residue sequences; and
    (e) cyclizing the second peptoid by chemically coupling a terminal residue of the second peptoid to the cyclizing residue of the second peptoid,
    wherein said first peptoid is linear peptoid and said second peptoid is a cyclized peptoid.

2. The method of claim 1, wherein the cyclizing residue and the attachment group are coupled by a linker.

3. The method of claim 1, wherein the support is a peptoid primed support.

4. The method of claim 1, wherein the support is a bead.

5. The method of claim 4, wherein the bead is a Rink-amide bead.

6. The method of claim 1, wherein the cyclizing residue comprises a side chain that is reactive with the terminal peptoid residue.

7. The method of claim 6, wherein the cyclizing residue comprises a side chain having a —COOH group.

8. The method of claim 7, wherein the cyclizing residue is glutamic acid or aspartic acid residue.

9. The method of claim 1, further comprising, prior to step (e), adding a 2-methoxyethylamine (Nmea), 1-(3-(aminopropyl)-2-pyrrolidinone (Napp), isobutylamine (Nleu), cyclohexylamine (Nch), or 3-methoxypropylamine (Nmpa) group as the terminal group of the first and second peptoids.

10. The method of claim 1, further comprising cleaving the second peptoid from the support.

11. The method of claim 10, further comprising immobilizing a plurality of cleaved second peptoids on an array support by coupling the array attachment group on the array support.

12. The method of claim 11, further comprising contacting the plurality of second peptoids on an array with a binding target and identifying a second peptoid the binds the binding target.

13. The method of claim 12, further comprising sequencing said first peptoid to determine the sequence of the second peptoid that binds the binding target.

* * * * *

UNITED STATES PATENT AND TRADEMARK OFFICE
CERTIFICATE OF CORRECTION

PATENT NO. : 8,759,259 B2
APPLICATION NO. : 12/905605
DATED : June 24, 2014
INVENTOR(S) : Yong-Uk Kwon and Thomas Kodadek It is certified that error appears in the above-identified patent and that said Letters Patent is hereby corrected as shown below:

In title page, item (56) References Cited - Other Publications, delete the 1st reference on page 1 "Gocke et al., "Supplemental Data-Isolation of antagonists of antigen-specific autoimmune T cell proliferation," *Chemistiy & Biology*, 16:1133-1139, 2009." and replace with --Gocke et al., "Supplemental Data-Isolation of antagonists of antigen-specific autoimmune T cell proliferation," *Chemistry & Biology*, 16:1133-1139, 2009.-- therefor.

In title page, item (56) References Cited - Other Publications, delete the 16th reference on page 4 "Robinson et al., "Autoantigen microarrays for multiplex characterization of autoantibody responsesm," *Nature Medicine*, 8:295-301, 2002." and replace with --Robinson et al., "Autoantigen microarrays for multiplex characterization of autoantibody responses," *Nature Medicine*, 8:295-301, 2002.-- therefor.

In title page, item (56) References Cited - Other Publications, delete the 32nd reference on page 4 "Tannapfel et al., "Identification of novel proteins associated with hepatocellular carcinomas using protein microarrays," *J. of Pathology*, 238-249, 2003." and replace with --Tannapfel et al., "Identification of novel proteins associated with hepatocellular carcinomas using protein microarrays," *J. of Pathology*, 201:238-249, 2003.-- therefor.

In title page, item (56) References Cited - Other Publications, delete the 33rd reference on page 4 "Terryberry et al., "Autoantibodies in Neurogdegenerative Diseases: Antigen-Specific Frequencies and Intrathecal Analysis," *Neurobiology of Aging*, 19:205-216." and replace with --Terryberry et al., "Autoantibodies in Neurodegenerative Diseases: Antigen-Specific Frequencies and Intrathecal Analysis," *Neurobiology of Aging*, 19:205-216, 1998.-- therefor.

In title page, item (56) References Cited - Other Publications, delete the 34th reference on page 4 "Terskikh et al., "'Peptabody3 : A new type of high avidity binding protein," *Proc. Natl. Acad. Sci., USA*, 94:1663-1668, 1997." and replace with --Terskikh et al., "'Peptabody': A new type of high avidity binding protein," *Proc. Natl. Acad. Sci., USA*, 94:1663-1668, 1997.-- therefor.

Signed and Sealed this
Seventh Day of October, 2014

Michelle K. Lee
*Deputy Director of the United States Patent and Trademark Office*

CERTIFICATE OF CORRECTION (continued)
U.S. Pat. No. 8,759,259 B2

In title page, item (56) References Cited - Other Publications, delete the 41st reference on page 4 "Veenstra and Com-ads, "Serum protein fingerprinting," *Curr. Opin. Mol. Therapeutics,* 15:584-593, 2003." and replace with --Veenstra and Conrads, "Serum protein fingerprinting," *Curr. Opin. Mol. Therapeutics*, 15:584-593, 2003-- therefor.

In title page, item (56) References Cited - Other Publications, delete the 24th reference on page 5 "Satoh. et al., "Synthetic peptides derived from the fourth domain of CD4 antagonize off function and inhibition T cell activation," *Biochem. Biophys. Res. Commun.*, 224:433-43, 1996." and replace with --Satoh, et al., "Synthetic peptides derived from the fourth domain of CD4 antagonize off function and inhibition T cell activation," *Biochem. Biophys. Res. Commun.*, 224:438-43, 1996.-- therefor.

In title page, item (56) References Cited - Other Publications, delete the 26th reference on page 5 "Udugamasooriya and Spaller, "Conformatinal constraint in protein ligand design and the inconsistency of binding entropy," *Biopolymers*, 89:653-67, 2008." and replace with --Udugamasooriya and Spaller, "Conformational constraint in protein ligand design and the inconsistency of binding entropy," *Biopolymers*, 89:653-67, 2008.-- therefor.

In title page, item (56) References Cited - Other Publications, delete the 27th reference on page 5 "Uttamchandani, et al., "Small molcule microarrays recent advances and applications," *Curr. Opin. Chem. Biol.*, 9:4-13, 2005." and replace with --Uttamchandani, et al., "Small molecule microarrays: recent advances and applications," *Curr. Opin. Chem. Biol.*, 9:4-13, 2005.-- therefor.

In the Claims

In claim 12, column 28, line 33, delete the first occurrence of "the" and replace with --that-- therefor.